US008426558B2

(12) United States Patent
Middleton-Hardie et al.

(10) Patent No.: US 8,426,558 B2
(45) Date of Patent: *Apr. 23, 2013

(54) PEPTIDE COMPOSITION AND A METHOD OF PROMOTING CARTILAGE FORMATION

(75) Inventors: Catherine Middleton-Hardie, Hayward, CA (US); Mirella Lazarov, Hayward, CA (US); David Rosen, Hayward, CA (US)

(73) Assignee: OrthoTrophix, Inc., Foster City, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 12/968,532

(22) Filed: Dec. 15, 2010

(65) Prior Publication Data

US 2011/0105401 A1    May 5, 2011

Related U.S. Application Data

(63) Continuation of application No. 12/018,080, filed on Jan. 22, 2008, now Pat. No. 7,888,462.

(60) Provisional application No. 60/885,961, filed on Jan. 22, 2007, provisional application No. 60/940,057, filed on May 24, 2007, provisional application No. 60/969,052, filed on Aug. 30, 2007.

(51) Int. Cl.
*C07K 14/00* (2006.01)

(52) U.S. Cl.
USPC .......... 530/324; 530/326; 514/16.8; 514/21.3

(58) Field of Classification Search .................. 530/324, 530/325, 326; 514/16.8, 21.3
See application file for complete search history.

(56) References Cited

U.S. PATENT DOCUMENTS

| | | | |
|---|---|---|---|
| 5,015,628 A | 5/1991 | Reynolds | |
| 5,407,644 A | 4/1995 | Rytter et al. | |
| 5,837,674 A | 11/1998 | Kumagai et al. | |
| 5,849,865 A | 12/1998 | Cheng et al. | |
| 5,853,746 A | 12/1998 | Hunziker | |
| 6,027,592 A | 2/2000 | Tseng et al. | |
| 6,045,780 A | 4/2000 | Bixler et al. | |
| 6,146,655 A | 11/2000 | Ruben | |
| 6,300,062 B1 | 10/2001 | Cerny et al. | |
| 6,329,357 B1 | 12/2001 | Norman et al. | |
| 6,673,900 B2 | 1/2004 | Rowe | |
| 6,790,639 B2 | 9/2004 | Brown et al. | |
| 6,911,425 B2 | 6/2005 | Kumagai et al. | |
| 7,078,021 B2 | 7/2006 | Yoneda et al. | |
| 7,135,459 B2 | 11/2006 | Deisher et al. | |
| 7,160,862 B2 | 1/2007 | Kumagai et al. | |
| 7,491,691 B2 | 2/2009 | Sindrey et al. | |
| 2002/0102641 A1 | 8/2002 | Schia, VI et al. | |
| 2002/0197267 A1 | 12/2002 | Kumagai et al. | |
| 2003/0166239 A1 | 9/2003 | Brown et al. | |
| 2005/0002875 A1 | 1/2005 | Yoneda et al. | |
| 2006/0210493 A1 | 9/2006 | Yoneda et al. | |

FOREIGN PATENT DOCUMENTS

| | | |
|---|---|---|
| EP | 1 400 252 | 3/2004 |
| WO | 95/14714 | 6/1995 |
| WO | 99/08730 | 2/1999 |
| WO | 99/48909 | 2/1999 |
| WO | 99/43844 | 9/1999 |
| WO | 99/60017 | 11/1999 |
| WO | 00/52041 | 9/2000 |
| WO | 01/72826 | 10/2001 |
| WO | 02/05836 | 1/2002 |
| WO | 02/14360 | 2/2002 |
| WO | 03/066666 | 8/2003 |
| WO | 2007/011610 | 1/2007 |

OTHER PUBLICATIONS

Nagel et al., "A fragment of the hypophosphatemic factor, MEPE, requires inducible cyclooxygenase-2 to exert potent anabolic effects on normal human marrow osteoblast precursors" Journal of Cellular Biochemistry (Dec. 2004) 93(6):1107-1114.
Kawasaki et al. (1995) "Calcium-Binding Proteins 1: EF-hands." Protein Profile, vol. 2(4):305-356.
Kimmel-Jehan et al., "Cloning of the mouse 25-hydroxyvitamin D3-1.alpha.-hydroxylase (CYP1.alpha.) gene" Biochimica et Biophysica Acta, 1475:109-113 (2000).
Lajeunesse et al., "Direct demonstration of a humorally-mediated inhibition of renal phosphate transport in the Hyp mouse" Kidney International 50:1531-1538 (1996).
Lopez-Moratalla et al., "A common structural motif in immunopotentiating peptides with sequences present in human autoantigens. Elicitation of a response mediated by monocytes and Th1 cells" Biochimica et Biophysica Acta, vol. 1317, No. 3, 1996, pp. 183-191.
Lufkin et al., (1994) "Pamidronate: an unrecognized problem in gastrointestinal tolerability." Osteoporos. Int., 4(6):320-322.
Martin et al., "Strategies to Minimize Bone Disease in Renal Failure" American Journal of Kidney Diseases, 38(6):1430-1436 (2001).
Meyer et al., "The Renal Phosphate Transport Defect in Normal Mice Parabiosed to X-Linked Hypophosphatemic Mice Persists After Parathyroidectomy" Journal of Bone and Mineral Research, 4(4):523-532 (1989).
Meyer et al., "Parabiosis Suggests a Humoral Factor Is Involved in X-Linked Hypophsphatemia in Mice" Journal of Bone and Mineral Research, 4(4):493-500 (1989).
Miller et al., "Genetics of vitamin D biosynthesis and its disorders" Best Practice & Research Clinical Endocrinology and Metabolism, 15(1):95-109 (2001).

(Continued)

*Primary Examiner* — David Lukton
(74) *Attorney, Agent, or Firm* — Karl Bozicevic; Bozicevic, Field & Francis LLP

(57) ABSTRACT

The present invention is a peptide compound which stimulates the formation of hard tissues such as bone and cartilage. The invention is also related to a method to treat a defect in hard tissues such as bone and cartilage using the peptide. The method of the present invention may be used to treat or prevent the defects in bones and cartilages which are caused by rheumatoid arthritis or osteoarthritis which involves the regeneration of new bone or cartilage in or around the defects.

7 Claims, 6 Drawing Sheets

OTHER PUBLICATIONS

Moncrief et al. (1990) "Evolution of EF-Hand Calcium-Modulated Proteins. I. Relationships Based on Amino Acid Sequences." J. Mol. Evol., vol. 30:522-562.

Morgan et al., "Renal Transplantation in Hypophsphatemia With Vitamin D-Resistant Rickets" Arch. Intern. Med., 134:549-552 (1974).

Muller et al., "1.alpha.,25-Dihydroxyvitamin D3 and a novel vitamin D analogue MC 903 are potent inhibitors of human interleukin 1 in vitro" Immunology Letters, 17:361-366 (1988).

Mundy et al., (1999) "Stimulation of bone formation in vitro and in rodents by statins." Science, 286:1946-1949.

Nesbitt et al., "Crosstransplantation of Kidneys in Normal and Hyp Mice" J. Clin. Invest. 89:1453-1459 (1992).

Nesbitt et al., "Phosphate Transport in Immortalized Cell Cultures from the Renal Proximal Tubule of Normal and Hyp Mice: Evidence That the HYP Gene Locus Product Is an Extrarenal Factor" Journal of Bone and Mineral Resesarch, 10(9):1327-1333 (1995).

Nesbitt et al., "Normal Phosphate Transport in Cells from the S2 and S3 Segments of Hyp-Mouse Proximal Renal Tubules" Endocrinology, 137(3):943-948 (1996).

Nesbitt et al., "Abnormal Parathyroid Hormone-Realted Peptide Formulation of Renal 25-Hydroxyvitamin D-1-Hydroxylase In Hyp Mice: Evidence for a Generalized Defect of Enzyme Activity in the Proximal Convoluted Tubule" Endocrinology, 127(2):843-848 (1990).

Petersen et al., "Identification of Osteoblast/Osteocyte Factor 45 (OF45), a Bone-specific cDNA Encoding an RGD-containing Protein That Is Highly Expressed in Osteoblasts and Osteocytes" The Journal of Biological Chemistry, 275(46):36172-36180 (2000).

Qiu et al., "Parental origin of mutant allele does not explain absence of gene dose in X-linked Hyp mice" Gene Res. Camb., 62:39-43 (1993).

Rowe et al., "Distribution of mutations in the PEX gene in families with X-linked hypophosphataemic rickets (HYP)" Human Molecular Genetics 6(4):539-549 (1997).

Rowe, "The role of the PHEX gene (PEX) in families with X-linkd hypophosphataemic rickets" Mineral Metabolism, 367-376 (1998).

Rowe, "The PEXGene: Its Role in X-Linked Rickets, Osteomalacia, and Bone Mineral Metabolism" Experimental Nephrology, 5:355-363 (1997).

Rowe et al., "Candidate 56 and 58 kDa Protein(s) Responsible for Mediating the Renal Defects in Oncogenic Hypophosphatemic Osteomalacia" Bone, 18(2):159-169 (1996).

Rowe et al., (2000) "MEPE, a new gene expressed in bone marrow and tumors causing osteomalacia." Genomics, 67:54-68.

Rowe, Peter S.N., "The role of the PHEX gene (PEX) in families with X-linked hypophosphataemic rickets" Current Opinion in Nephrology and Hypertension (1998) 7:367-376.

Rowe et al., (2004) "MEPE has the properties of an osteoblastic phosphatonin and minhibin" 34:303-319.

Schafer et al. (1995) "Isolation of a YAC Clone Covering a Cluster of Nine S100 Genes on Human Chromosome 1q21: Rationale for a New Nomenclature of the S100 Calcium-Binding Protein Family." Genomics, vol. 25:638-643.

Schneider et al., (1995) "Does HRT modify risk of gynecological cancers?" Int. J. Fertil. Menopausal Study, 40(1):40-53.

Stubbs et al., "Characterization of Native and Recombinant Bone Sialoprotein: Delineation of the Mineral-Binding and Cell Adhesion Domains and Structural Analysis of the RGD Domain" Journal of Bone and Mineral Research, 12 (8):1210-1222 (1997).

Takeyama et al., "25-Hydroxyvitamin D3 1.alpha.-Hydroxylase and Vitamin D Synthesis" Science, 277:1827-1830 (1997).

Traianedes et al., (1998) "5-Lipoxygenase metabolites inhibit bone formation in vitro." Endocrinology, 139:3178-3184.

Yang et al., "Peptide analogs from E-cadherin with different calcium-binding affinities" J. Peptide Res., 55:203-215 (2000).

Yoshida et al., "Identification of a Renal Proximal Tubular Cell-Specific Enhancer in the Mouse 25-Hydroxyvitamin D 1.alpha.-Hydroxylase Gene" J. Am. Soc. Nephrol., 13:1455-1463 (2002).

Yoshida et al., "Mediation of Unusually High Concentrations of 1,25-Dihydroxyvitamin D in Homozygous klotho Mutant Mice by Increased Expression of Renal 1.alpha.-Hydroxylase Gene" Endocrinology, 143(2):683-689 (2002).

Zehnder et al., J. Clin. Endocrinol. Metab., 86(2):888-894 (2001).

Zoidis et al., "Phex cDNA cloning from rat bone and studies on Phex mRNA expression: tissue-specificity, age-dependency, and regulation by insulin-like growth factor (IGF) I in vivo" Molecular and Cellular Endocrinology, 168:41-51 (2000).

Abe et al., "Differentiation of mouse myeloid leukemia cells induced by 1.alpha.,25-dihydroxyvitamine D3" PNAS, 78(8):4990-4994 (1981).

Bairoch et al. (1990) "EF-hand motifs in inositol phospholipid-specific phospholipase C." FEBS, vol. 269 (2):454-456.

Bikle, "Vitamin D: New Actions, New Analogs, New Therapeutic Potential; Update 1995" Endocrine Review, 4(1):77-83 (1995).

Brenza et al., "Parathyroid hormone activation of the 25-hydroxyvitamine D3-1.alpha.-Hydroxylase gene promoter" PNAS 95:1387-1391 (1998).

Carpenter, "New Perspectives on the Biology and Treatment of X-Linked Hypophsphatemic Rickets" Pediatric Endocrinology 44(2):443-465 (1997).

Carswell, "The Potential for Treating Neurodegenerative Disorders with NGF-Inducing Compounds" Experimental Neurology, 124:36-42 (1993).

Chappard et al., (1995) "Effects of tiludronate on bone loss in paraplegic patients." Journal of Bone and Mineral Research, 10(1):112-118.

Chauvaux et al. (1990) "Calcium-binding affinity and calcium-enhanced activity of Clostridium thermocellum endoglucanase D." Biochem. J., vol. 265:261-265.

Davis (1990) "The many Faces of Epidermal Growth Factor Repeats." The New Biologist, vol. 2(5):410-419.

Ecarot et al., "Defective Bone Formation by Hyp Mouse Bone Cells Transplanted into Normal Mice: Evidence in Favor of an Intrinsic Osteoblast Defect" Journal of Bone and Mineral Research, 7:215-200 (1992).

Ecarot et al., "Effect of 1,25-Dihydroxyvitamin D3 Treatment on Bone Formation by Transplanted Cells from Normal and X-Linked Hypophosphatemic Mice" Journal of Bone and Mineral Research, 10:424-431 (1995).

Economou et al. (1990) "The Rhizobium nodulation gene nodO encodes a Ca2+ -binding protein that is exported without N-terminal cleavage and is homologous to haemolysin and related proteins." The EMBO Journal, vol. 9(2):349-354.

Eto et al., "Assay of 25-Hydroxyvitamin D3 1.alpha.-Hydroxylase in Rat Kidney Mitochondria" Analytical Biochemistry, 258:53-58 (1998).

Ferris D. M. et al., "RGD-coated titanium implants stimulate increased bone formation in vivo" Biomaterials, Vo. 20, No. 23-24, Dec. 1999. pp. 2323-2331.

Fisher et al., "Inhibition of Osteoclastic Bone Resorption in Vivo by Eschistatin an "Arginyol-Glycyl-Aspartyl" (RGD)-Containing Protein" Endocrinology, 132(3):1411-1413 (1993).

Fratzl et al., (1994) "Abnormal bone mineralization after fluoride treatment in osteoporosis: a small-angle x-ray-scattering study." Journal of Bone and Mineral Research, 9(10):1541-1549.

Gennari et al., (1994) "Management of osteoporosis and Paget's disease. An appraisal of the risks and benefits of drug treatment." Drug Saf., 11(3):179-95.

George et al., "Characterization of a Novel Dentin Matrix Acidic Phosphoprotein" The Journal of Biological Chemistry, 268(17):12624-12630 (1993).

Gronowicz et al., (1994) "Synthetic peptide containing Arg-Gly-Asp inhibits bone formation and resorption in a mineralizing organ culture system of fetal rat parietal bones." Journal of Bone and Mineral Research, 9(2):193-201.

Hayashibara T. et al., "A synthetic peptide fragment of human MEPE stimulates new bone formation in vitro and in vivo" Journal of Bone and Mineral Research, New York, NY., US, vol. 19, No. 3, Mar. 2004, pp. 455-462.

Hewison et al., "1.alpha.-Hydroxylase and the action of vitamin D" Journal of Molecular Endocrinology, 25:141-148 (2000).

Hilfiker, (1998) "Characterization of a murine type II sodium-phosphate cotransporter expressed in mammalian small intestine." Proc. Natl. Acad. Sci. USA, 95(24):14564-14569.

Horton et al., "Arg-Gly-Asp (RGD) Peptides and the Anti-Vitronectin Receptor Antibody 23C6 Inhibit Dentine Resorption and Cell Spreading by Osteoclasts" Experimental Cell Research, 195:368-375 (1991).

Inomata et al., "Effect of 1.alpha.(OH)-vitamin D3 on insulin secretion in diabetes mellitus" Bone and Mineral, 1:187-192 (1986).

Kato et al., "Molecular Genetics of Vitamin D-Dependent Hereditary Rickets" Hormone Research, 57:73-78 (2002).

PEPTIDE COMPOSITION AND A METHOD OF PROMOTING CARTILAGE FORMATION

CROSS REFERENCE

This application is a continuation of U.S. patent application Ser. No. 12/018,080 filed Jan. 22, 2008, U.S. Pat. No. 7,888,462 which claims the benefit of U.S. Provisional Application No. 60/885,961, filed Jan. 22, 2007; U.S. Provisional Application No. 60/940,057, filed May 24, 2007; and U.S. Provisional Application No. 60/969,052, filed Aug. 30, 2007, all of which applications are incorporated herein by reference.

BACKGROUND

Bone Formation

Bones in mammals form the skeleton of the bodies which not only gives their structural shape but supports the mechanical burden of the bodies.

A defect in the bones such as a bone breakage causes a variety of mortality and morbidity problems unless it is adequately treated in a timely fashion. Otherwise, such damaged bones retaining the defects become more difficult to repair at a later time or the damage may be even worsened as time passes.

Currently, the treatment of such bone defects largely relies on various medical devices including artificial bones and the natural healing process. A very limited therapeutic agent is available for re-building the damaged bones. Thus, efforts have been made to identify a new bone growth factor.

As a result, several molecules have been identified and claimed to have bone forming activities. However, only a few of them have been actually developed and commercially used as therapeutic agents.

An example of the available therapeutic agent which is able to stimulate new bone formation is a group of growth factor molecules named bone morphogenetic proteins, or BMPs that belong to a broader superfamily of transforming growth factor β (TGFβ). Several BMP molecules are known to stimulate differentiation, maturation, and mineralization of the bone cells to stimulate new bone formation. However, because of their non-selective bone formation activities on the soft tissues called ectopic ossification or ectopic calcification, they cannot be administered to other tissues than the bones. Thus, BMP molecules need to be used with a carrier material that is directly implantable into the bone defect so that the therapeutic BMP molecules can be applied only to the hard tissues without causing ectopic ossification or calcification in the surrounding soft tissues. Among BMPs, BMP-2 has been approved as a medical product in combination with a carrier material that is implanted into the defects in the bones. However, the product (Infuse®) is used alone as a therapeutic agent because of its ectopic ossification activities.

To overcome the ectopic ossification or calcification problems, further efforts have been made to identify a new bone growth factor that has specificity and selectivity only to the bones. One of the molecules identified from such efforts was AC-100 or Dentonin®. AC-100 or Dentonin® was identified as a small fragment within a large molecule named MEPE (matrix extracellular phosphoglycoprotein) and has demonstrated to stimulate proliferation, differentiation, and mineralization of human osteoblastic cells (Nigel, et. al., Journal of Cellular Biochemistry 2004; 93(6): 1107-1114; U.S. Pat. Nos. 6,911,425; 7,078,021 and 7,160,862). AC-100 has also shown bone formation activities in vivo (Hayashibara, et. al., Journal of Bone and Mineral Research 2004; 19(3):455-462; Lazarov, et. al., ASBMR Abstract, 2004). AC-100 or Dentonin® has demonstrated stimulation of the proliferation of human dental pulp cells in vitro (Liu et al., Journal of Dental Research 2004; 83(6):496-499) and formation of new dentin in a dental defect in human in its clinical trial (Lazarov et. al., IADR Abstract, 2006).

AC-100 is characteristic in that it contains a few unique motifs such as an RGD integrin-binding motif and a SGDG glycosaminoglycan motif and these motifs are believed to give the molecule a structure that is essential for its bioactivities.

It was also believed that the hard tissue formation activities possessed by AC-100 were limited to bone and dentin in teeth.

Osteoarthritis

Osteoarthritis (OA) is a degenerative disease and is the most common form of arthritis (National Institute of Arthritis and Musculoskeletal and Skin Diseases (NIAMS), National Institutes of Health (NIH)). It can affect cartilage in any part of the body, but is most common in hips and knees, and to a lesser extent the fingers. Unlike rheumatoid arthritis (RA), the incidence of OA typically increases with age. The specific cause of the disease is unclear, but is often linked to degeneration over time due to excessive wear and tear on joints. This can lead to a local inflammation which in turn slowly starts to erode the cartilage. OA can occur in young people also where the degenerative process is accelerated due to a physical injury (Buckwalter et al., J Orthop Sports Phy Ther 1998; 28:192).

Unlike bone, cartilage is not able to effectively repair itself (Mankin, J., Bone Joint Surg [Am] 1982; 64A:460) (Hunziker, Clin Othop 1999; 367:135). Therefore, once this degenerative process has begun, there is little that can be done to reverse it. However, there has been a renewed interest in cartilage biology which has resulted in potential new therapeutic approaches. Currently however, most treatment options are aimed at addressing the pain associated with the disease or slowing the disease progression. Some surgical options exist with variable success in achieving temporary repair. These options, however, often result in the degenerative process being delayed but not halted. Continued degeneration continues until the cartilage and underlying bone is destroyed, resulting in the need for a joint replacement (American Academy of Orthopaedic Surgeons (AAOS)).
Current Therapeutic Options:

Currently, there is no cure for osteoarthritis and no way to reverse the damage that it causes. Reduction in joint stress through change in physical activity or weight loss is usually recommended to reduce the rate of joint degradation. Pharmacologic treatment options such as acetaminophen, NSAIDs and selective cyclooxygenase-2 (COX-2) inhibitors address the pain associated with OA but only provide temporary pain relief and are not disease modifying. In addition, steroids can also be injected directly into the joints and surrounding synovial fluid, but again they only provide pain relief and no modification of disease progression. Injection of viscous material into the synovial fluid space is also a treatment option. Hyaluronic acid (HA) has been used with varying degrees of success to lubricate joints. HA products are administered over several injections and will aid in reduction of joint pain for a few months but will not reverse the damage caused by OA.

There have also been some studies suggesting that food supplements such as glucosamine and/or chondroitin may relieve symptoms of pain associated with osteoarthritis.

These supplements are widely available without a prescription. There have been few, if any well controlled clinical trials evaluating the effectiveness of these agents. The National Institutes of Health (NIH) has been studying glucosamine and chondroitin in the treatment of osteoarthritis. Initial research has demonstrated only a minor benefit in relieving pain for those with the most severe osteoarthritis. Further studies should clarify the potential benefits of these types of products.

To address the underlying disease, some form of surgical procedure is usually required. In cases where there is a chronic inflammation, the inflamed tissue (synovium) can sometimes be removed in an effort to stop the inflammation and further degeneration. There are arthroscopic techniques utilized to reduce joint pain or initiate some repair (Hayes et al., Bone Cart Wound Heal 2001; 18:35) (Beris et al., 2005; 36S:S14). Arthroscopic debridement and lavage removes loose and ragged cartilage, and is a common procedure to reduce joint pain (Jackson et al., Arthroscopy 2003; 19:13). However, there is no evidence of any promotion of cartilage repair. Other arthoscopic techniques such as drilling and microfractures involve drilling holes (2-2.5 mm or 0.5-1 mm respectively) through the cartilage into the subchondral bone. Exposure of the subchondral bone and contact with mesenchymal stem cells results in filling of the defects with either fibrocartilage (large holes) or a mix of hyaline and fibrocartilage (smaller holes) (Steadman et al., Oper Technol Orthop 1997; 7:300). There has also been a renewed interest in repair of existing cartilage. Mosaicplasty is also performed in the form of osteochondral grafts. Osteochondral allografts are used to fill large full thickness defects while autologous grafts are used for smaller full thickness defects (Czitrom et al., Clin Orthop 1986; 208:141). In autologous osteochondral transplantation a cylindrical osteochondral plug is removed from a non-weight bearing area of the joint and transferred into a debrided full thickness defect.

Cartilage cells (chondrocytes) grown in vitro have been successfully used to regenerate cartilage (autologous chondrocyte implantation: ACI) (Brittberg et al., Clin Orthop 1996; 326:270). This procedure involves two surgeries. The first involves harvest of healthy articular cartilage. The tissue is digested and chondrocytes isolated for culture to expand the cell number by 20-50 fold. In the second surgery, the damaged cartilage is cleared down to the subchondral bone. A separate incision is made in the medical tibia where a piece of periosteum is removed. The periosteal flap is sutured over the defect in combination with a fibrin glue. The cultured chondrocytes are injected into the defect. Over time, the chondrocytes proliferate and produce new cartilage matrix. While successful in a number of cases, this process is quite variable and depends on the availability of healthy autologous chondrocytes (usually from an unaffected joint). Studies comparing the efficacy of ACI and mosaicplasty have produced conflicting results (Horas et al., J Bone Joint Surg [Am] 2003; 83:185) (Bentley et al., J Bone Joint Surg [Br] 2003; 85:223). ACI procedures are very invasive and can only be used to treat small cartilage defects. Research involving the use of stem cells is also underway and may eventually provide an alternate method of cartilage repair via cell transplantation.

In most cases, however, OA ultimately requires a more severe procedure in the form of a joint replacement (e.g., hip or knee). In this procedure, the damaged cartilage is removed and replaced with a synthetic joint. The exact type of implant, and the method and location of the incisions, depend on the needs of the particular patient and the surgeon performing the procedure. Knee replacements (or arthroplasties) typically consist of a femoral component, a bibial component, and a patellar component. There are a large number of manufacturers and designs of knee prostheses. Most prostheses last at least 10 years and some of the newer implants can last up to 20 years.

In summary, although there have been significant advances in materials science and cartilage biology, there is still no satisfactory method to treat the cartilage damage resulting from OA.

SUMMARY

The invention includes a peptide compound and a formulation of the peptide with a pharmaceutically acceptable carrier, manufactured for use in the treatment of hard tissue (bone and cartilage). The peptide compound can be any of the peptides disclosed here (alone or in combination with each other) and the carrier can be an injectable solution and/or a solid biocompatible, biodegradable polymeric implant which may provide for controlled release of the peptide over an extended period of times e.g. 8 hours, 12 hours, 24 hours, 2 days, 5 days, 10 days or more.

The present invention relates to a group of peptides that are represented by a common amino acid sequence motif of DLXXXXXNDXXPFXXXXQXF (SEQ ID NO:1), wherein X is any amino acid. Multiple peptides sharing this common sequence are shown here to stimulate growth of hard tissues such as bone and cartilage.

In particular, a subgroup of the peptide of SEQ ID NO:1 which shares the common sequence motif of DLQEXXX-NDXSPFXXXXQPF (SEQ ID NO:2), wherein X is any amino acid is also disclosed. Multiple peptides sharing this common sequence are shown here to stimulate growth of hard tissues such as bone and cartilage.

In a further embodiment, a group of slightly larger peptides which also share the common sequence motif described above and further share a larger amino acid sequence motif of TDLQEXXXNDXSPFXXXXQPFKD (SEQ ID NO:3), wherein X is any amino acid is also disclosed. Multiple peptides sharing this common sequence are shown here to stimulate growth of hard tissues such as bone and cartilage.

The present invention also covers a method for promoting hard tissue formation, in particular, cartilage formation. It has been demonstrated that administration of a formulation comprising a therapeutically effective amount of a peptidic compound of this invention, including but not limited to TDLQERGDNDISPFSGDGQPFKD (SEQ ID NO:21) and a carrier material promoted formation of new cartilage in a defect in knee cartilage in a goat model.

An aspect of the invention includes a formulation comprising a pharmaceutically acceptable excipient and a peptide of DLXXXXXNDXXPFXXXXQXF (SEQ ID NO:1).

Another aspect of the invention is a pharmaceutical formulation comprising a pharmaceutically acceptable excipient and a peptide of

```
DLQEXXXNDXSPFXXXXQPF        (SEQ ID NO: 2)
or
TDLQEXXXNDXSPFXXXXQPFKD.    (SEQ ID NO: 3)
```

In another aspect of the invention is a method of treatment comprising determining a level of cartilage present in a target area, determining the level to be below normal, and administering to the subject a therapeutically effective amount of a formulation comprising a pharmaceutically acceptable excipient having therein a peptide of SEQ ID NO:1.

In another aspect of the invention is a method of treatment comprising determining a level of cartilage present in a target area, determining the level to be below normal, and administering to the subject a therapeutically effective amount of a formulation comprising a pharmaceutically acceptable excipient having therein a peptide of SEQ ID NO:2 or 3.

An aspect of the invention includes a formulation comprising a pharmaceutically acceptable excipient and a peptide of SEQ ID NO:1 wherein the substitutions for X as being any amino acid are such that the sequence is not the sequence of SEQ ID NO:21.

An aspect of the invention includes a formulation comprising a pharmaceutically acceptable excipient and a peptide of SEQ ID NO:2 or 3 wherein the substitutions for X as being any amino acid are such that the sequence is not the sequence of SEQ ID NO:21 but the sequences such as, for example, SEQ ID NO: 22, 23, 24, 25, 26, or 27.

An aspect of the invention includes a method for promoting cartilage by activating cyclooxygenase-2 (COX-2).

These and other aspects, objects, advantages, and features of the invention will become apparent to those persons skilled in the art upon reading the details of the subject invention, as more fully described below.

BRIEF DESCRIPTIONS OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

Figure 3:
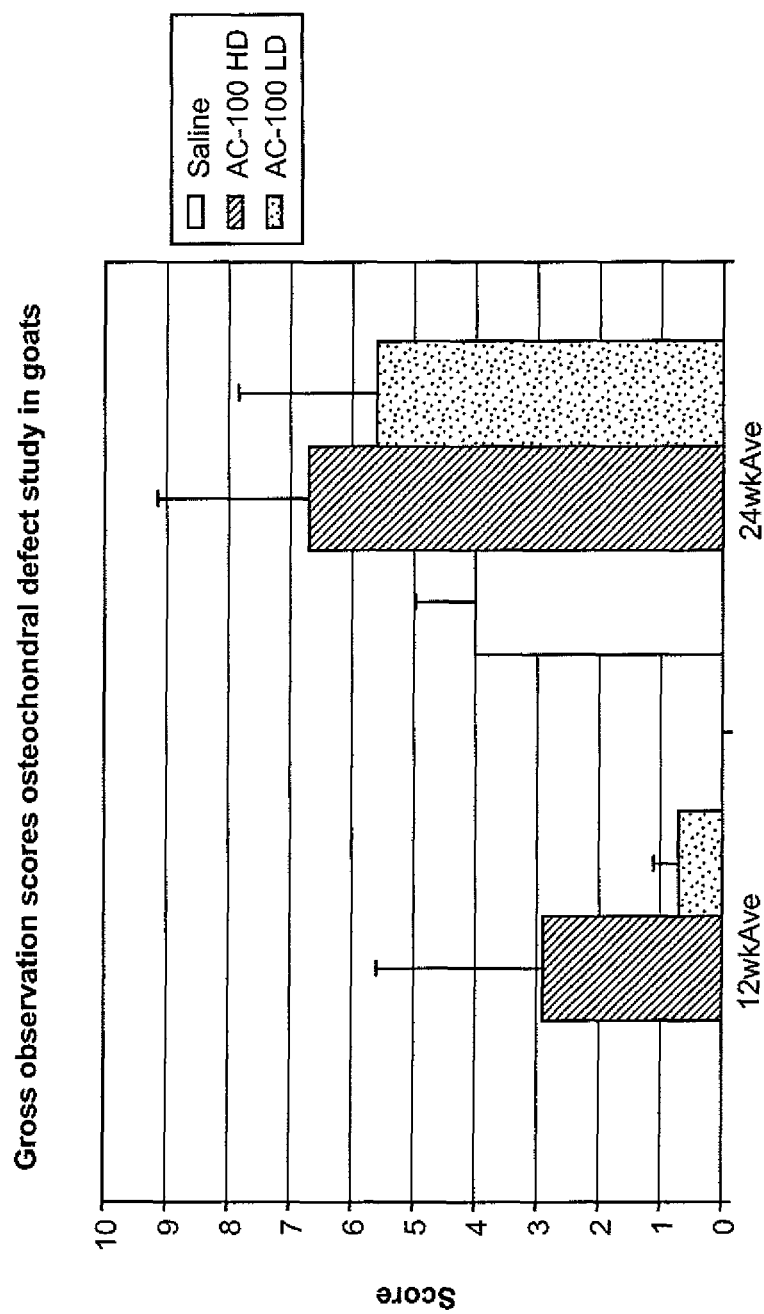

FIG. 3 is a bar graph that depicts morphological data demonstrating that AC-100 was able to increase the formation of cartilage during the first 12 weeks (84 days) and 24 weeks (168 days) of initial treatment, respectively. AC-100 at both 10 mg (4×2.5 mg) and 100 mg (4×25 mg) carried by collagen sponge stimulated the formation of cartilage in a goat osteoarthritis model. High and low doses of AC-100 were tested for their activities to heal the defects. The activities were dose dependent.

Figure 4:
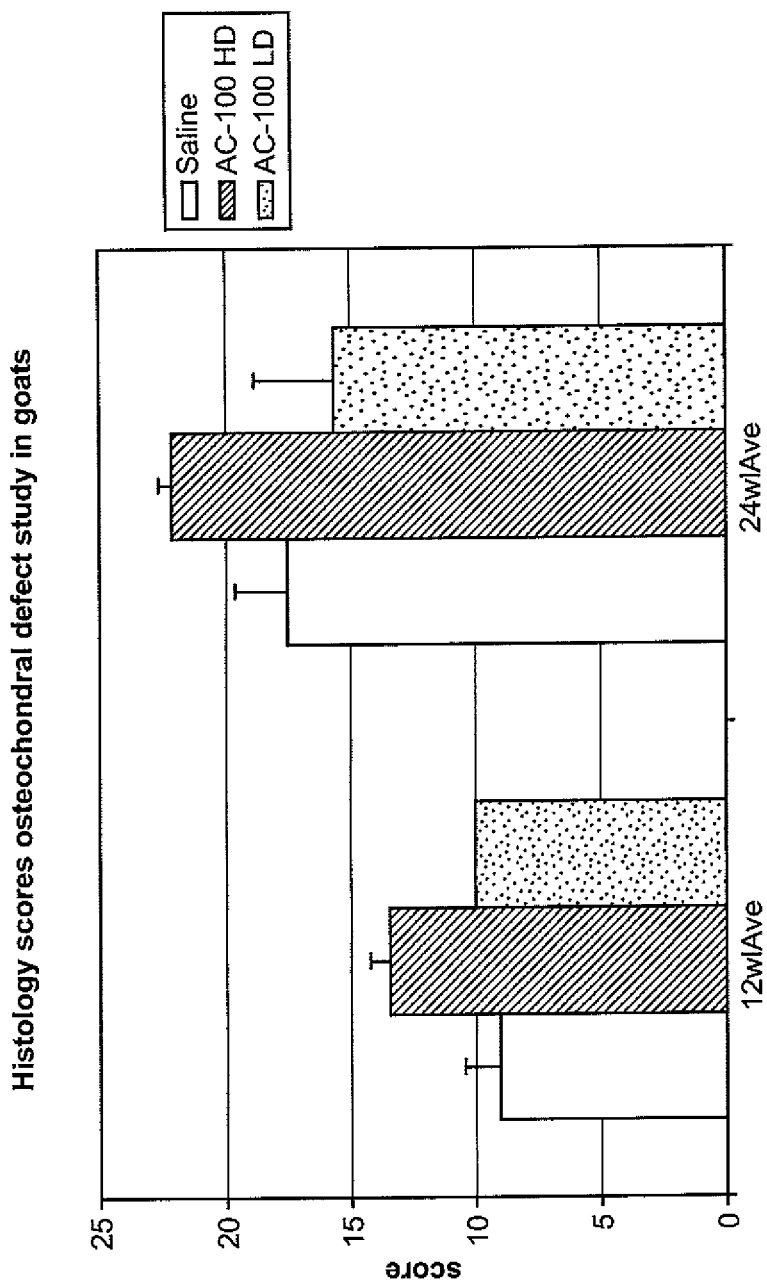

FIG. 4 is a bar graph that depicts histological data demonstrating that AC-100 was able to increase the formation of cartilage during the first 12 week (84 days) and 24 week (168 days) periods from the initial treatment, respectively. AC-100 at both 10 mg (4×2.5 mg) and 100 mg (4×25 mg) carried by collagen sponge stimulated the formation of cartilage in a goat osteoarthritis model. High and low doses of AC-100 were tested for their activities to heal the defects. The activities were dose dependent.

Figure 5:
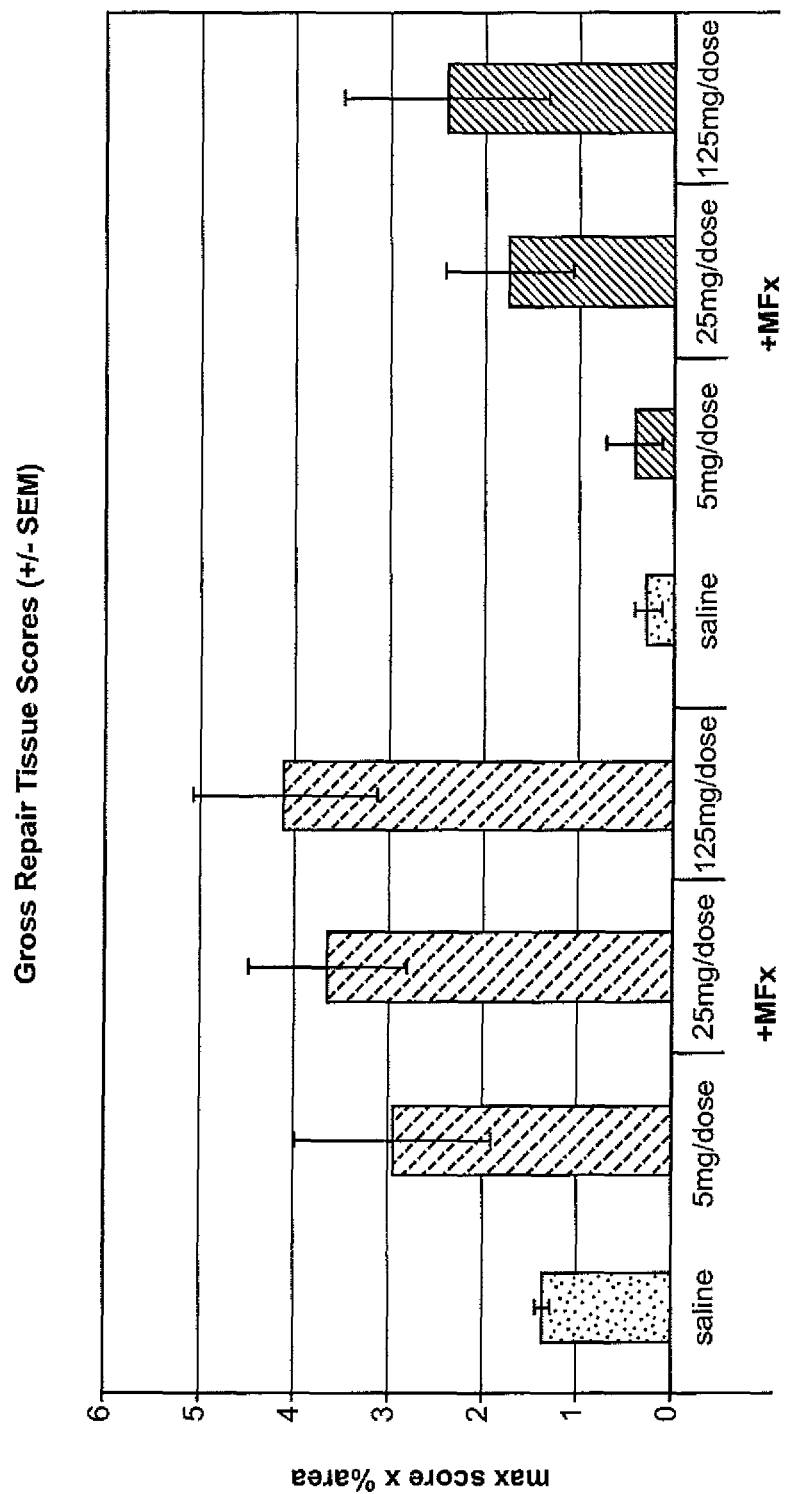

FIG. 5 is a bar graph that depicts gross tissue repair scores illustrating that a series of AC-100 intra-articular injections dose-dependently stimulates growth of new cartilage in a full-thickness cartilage defect after 6 weeks.

Figure 6:
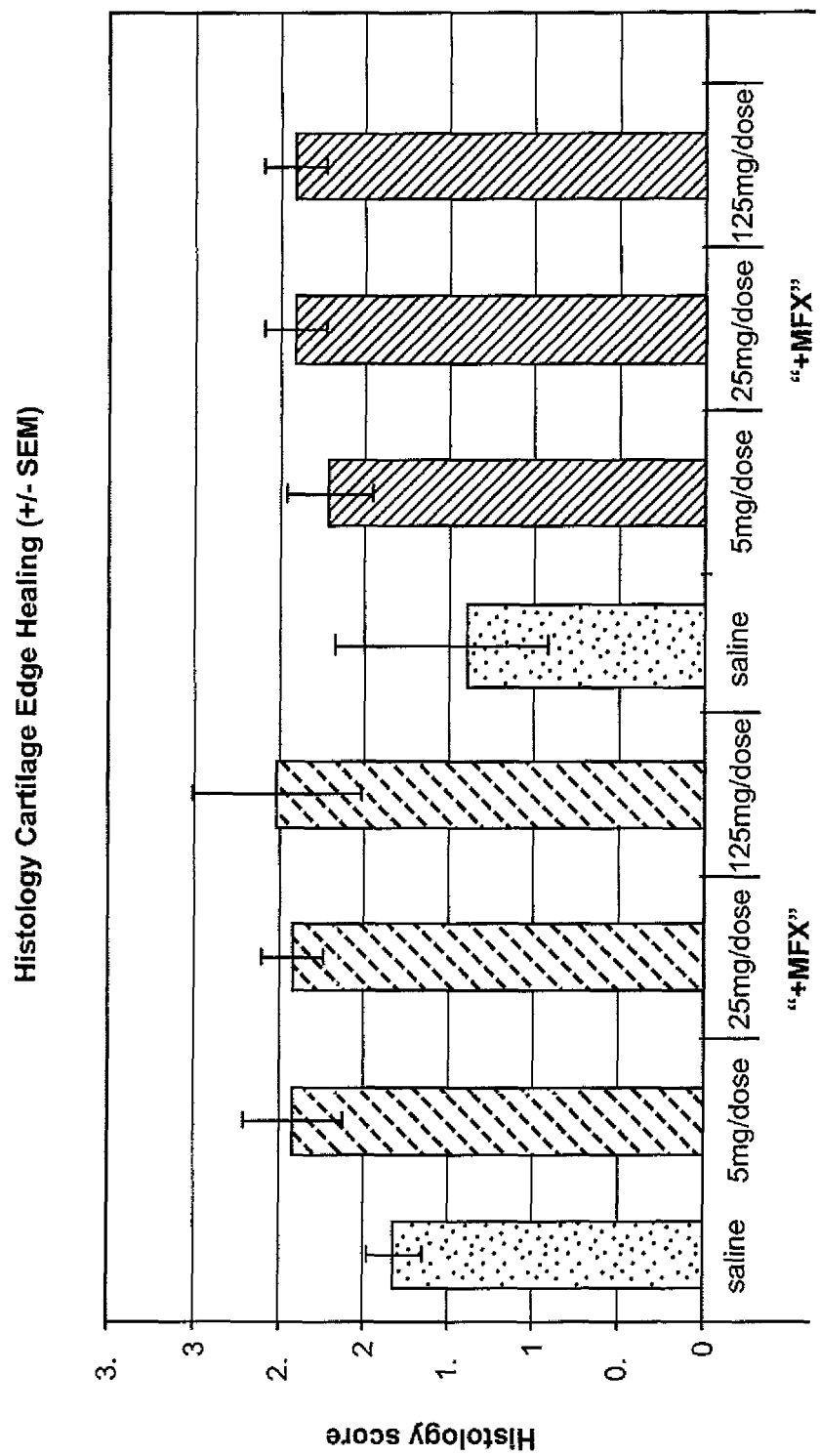

FIG. 6 is a bar graph that depicts histology scores illustrating the ability of AC-100 to dose-dependently increase the formation of cartilage repair tissue within a full-thickness cartilage defect when administered as a series of intra-articular injections.

DETAILED DESCRIPTION OF THE INVENTION

Before the methods, peptides, analogs, and formulations of the present invention are described, it is to be understood that this invention is not limited to any particular embodiment described, and as such may, of course, vary. It is also to be understood that the terminology used herein is with the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Previous work with AC-100 or Dentonin® has demonstrated that treatment of bone or bone cells results in an increase in an induction of COX-2 and prostaglandin E2 (PGE2) production. Two key enzymes involved in prostaglandin production are COX-1, which is constitutively produced and COX-2 which is increased in response to stimuli such as inflammatory cytokines. COX-2 is also highly expressed in both rheumatoid arthritis (RA) and osteoarthritis (OA) (Vane J R, Bakhle Y S, and Botting R M. Annual Rev. Pharmacol. Toxocol. 1998, 38:35-57 and Amin A R et al. J. Clin Invest. 1997, 99(6):1231-1237 respectively). The increase in COX-2 and subsequent PGE production is believed to be responsible for the pain and inflammation seen in these conditions. As such, many therapeutics currently used in the management of RA and OA are directed at inhibition of COX-2 and subsequent production of prostaglandins. Furthermore, there have been conflicting reports regarding the effects of NSAIDs and more specific COX-2 inhibitors on chondrocytes. NSAIDs and/or COX-2 inhibitors have been reported to induce apoptosis, inhibit proteoglycan synthesis, and stimulate production of chemokines in chondrocytes (Nakamura H et al., 2007, Clin. Exp Rheumatol. 25(1):11-16). Others have reported inhibition of proliferation of chondrocytes by NSAIDs but little effect on apoptosis by COX-2 inhibitors (Chang J K et al., 2006, Toxicology. 228(2-3):111-123). Although previously shown to induce COX-2, AC-100, in combination with a collagen sponge, was able to induce a reparative response in a goat model of OA despite previous reports that AC-100 can induce COX-2 and PGE2 synthesis. This unexpected finding is one the subject of the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent there is a contradiction between the present disclosure and a publication incorporated by reference.

It must be noted that as used herein and in the appended claims, the singular forms "a", "and", and "the" include plural referents unless the context clearly dictates otherwise. Thus, for example, reference to "a peptide" includes a plurality of such peptides and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "peptide" and "peptidic compound" are used interchangeably herein to refer to a polymeric form of amino acids of from about 10 to about 50 amino acids, (may consist of at least 20 and not more than 50 amino acids) which can comprise coded and non-coded amino acids, chemically or biochemically modified or derivatized amino acids, L- or D-amino acids, peptides having modified peptide backbones, and peptides comprising amino acid analogs. The peptidic compounds may be polymers of: (a) naturally occurring amino acid residues; (b) non-naturally occurring amino acid residues, e.g. N-substituted glycines, amino acid substitutes, etc.; or (c) both naturally occurring and non-naturally occurring amino acid residues/substitutes. In other words, the subject peptidic compounds may be peptides or peptoids. Peptoid compounds and methods for their preparation are described in WO 91/19735, the disclosure of which is herein incorporated by reference. A peptide compound of the invention may comprise or consist of 23 amino acids or from 18 to 28 amino acids or from 20 to 26 amino acids. The active amino acid sequence of the invention comprises or consists of three motifs which may be overlapping which are: an integrin binding motif sequence; a glycosaminoglycan binding motif sequence; and a calcium-binding motif.

The terms "treatment", "treating" and the like are used herein to generally mean obtaining a desired pharmacologic and/or physiologic effect, e.g., stimulation of angiogenesis. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing a disease or condition (e.g., preventing the loss of cartilage) from occurring in a subject who may be predisposed to the disease but has not yet been diagnosed as having it; (b) inhibiting the disease, e.g., arresting loss of cartilage; or (c) relieving the disease (e.g., enhancing the development of cartilage.

The term "antibody" is meant an immunoglobulin protein capable of binding an antigen. The term "antibody" as used herein is intended to include antibody fragments (e.g. F(ab')$_2$, Fab', and Fab) capable of binding an antigen or antigenic fragment of interest.

The term "binds specifically" is meant high avidity and/or high affinity binding of an antibody to a specific peptide— specifically a peptide of the invention. Antibody binding to its specific target epitope is stronger than the binding of the antibody to other epitopes on the peptide or to other epitopes on other peptides. Antibodies which bind specifically to a peptide of interest may be capable of binding to other peptides at a weak, yet detectable level (e.g. 10% or less of the binding shown to the peptide of interest). Such weak binding or background binding, is readily discernable from the specific antibody binding to the peptide of interest, e.g. by the use of appropriate controls.

The terms "subject," "individual," "patient," and "host" are used interchangeably herein and refer to any vertebrate, particularly any mammal and most particularly including human subjects, farm animals, and mammalian pets. The subject may be, but is not necessarily under the care of a health care professional such as a doctor.

Peptidic Compounds

Peptidic compounds of this invention are the peptides comprising from about 20 to 50 amino acids in their sequence and may consist of at least 20 and no more than 50 amino acids. The amino acids are preferably one of the twenty naturally occurring L-amino acids. However, D-amino acids may be present as may amino acid analogs.

A peptide of the current invention comprises a general amino acid sequence of DLXXXXXNDXXPFXXXXQXF (SEQ ID NO:1) and may consist only of this sequence. The peptides having this common sequence motif are shown here to have potent hard tissue formation activities in vitro and in vivo.

Specifically, the peptide of this invention comprises from about 20 to 50 amino acids in their sequence also comprising a general amino acid sequence of DLQEXXXNDXSPFXXXXQPF (SEQ ID NO:2) and may consist of only this sequence.

More specifically, the peptide of this invention comprises from about 21 to 35 amino acids in their sequence also comprising a general amino acid sequence of TDLQEXXXNDXSPFXXXXQPFKD (SEQ ID NO:3) and may consist of only this sequence. This larger general sequence (NO:3) contains the smaller general sequence indicated above, i.e., the second amino acid residue "D" through the 21$^{st}$ amino acid residue "F." The peptides having this common sequence motif have demonstrated potent hard tissue formation activities, such as bone and cartilage formation activities in vivo.

Individual amino acids may be present in the peptides in either the L or the D isoform, but preferably in the L form. A peptide of the invention can be amidated or non-amidated on its C-terminus, or carboxylated or non-carboxylated on its N-terminus.

Specific examples of the peptides of the invention which comprise the general amino acid sequence of DLXXXXX-NDXXPFXXXXQXF (SEQ ID NO:1) include the following:

| | |
|---|---|
| DLQERGDNDISPFSGDGQPF | (SEQ ID NO: 4) |
| DLQEDGRNDISPFSGDGQPF | (SEQ ID NO: 5) |
| DLQERGDNDISPFGDGSQPF | (SEQ ID NO: 6) |
| DLQEDGRNDISPFGDGSQPF | (SEQ ID NO: 7) |
| DLQERDGNDISPFSGDGQPF | (SEQ ID NO: 8) |
| DLQERGDNDISPFSDGDQPF | (SEQ ID NO: 9) |

-continued

| | |
|---|---|
| DLQERDGNDISPFSDGDQPF | (SEQ ID NO: 10) |
| DLQERWDNDISPFSGDGQPF | (SEQ ID NO: 11) |
| DLQERWDNDISPFGDGSQPF | (SEQ ID NO: 12) |
| DLQERGDNDMSPFSGDGQPF | (SEQ ID NO: 13) |
| DLQEDGRNDMSPFSGDGQPF | (SEQ ID NO: 14) |
| DLQERGDNDMSPFGDGSQPF | (SEQ ID NO: 15) |
| DLQEDGRNDMSPFGDGSQPF | (SEQ ID NO: 16) |
| DLLVRGDNDVPPFSGDGQHF | (SEQ ID NO: 17) |
| DLLVDGRNDVPPFSGDGQHF | (SEQ ID NO: 18) |
| DLLVRGDNDVPPFGDGSQHF | (SEQ ID NO: 19) |
| DLLVDGRNDVPPFGDGSQHF | (SEQ ID NO: 20) |
| TDLQERGDNDISPFSGDGQPFKD | (SEQ ID NO: 21) |
| TDLQEDGRNDISPFSGDGQPFKD | (SEQ ID NO: 22) |
| TDLQERGDNDISPFGDGSQPFKD | (SEQ ID NO: 23) |
| TDLQEDGRNDISPFGDGSQPFKD | (SEQ ID NO: 24) |
| TDLQERDGNDISPFSGDGQPFKD | (SEQ ID NO: 25) |
| TDLQERGDNDISPFSDGDQPFKD | (SEQ ID NO: 26) |
| TDLQERDGNDISPFSDGDQPFKD | (SEQ ID NO: 27) |
| TDLQERWDNDISPFSGDGQPFKD | (SEQ ID NO: 28) |
| TDLQERWDNDISPFGDGSQPFKD | (SEQ ID NO: 29) |
| TDLQERGDNDMSPFSGDGQPFKD | (SEQ ID NO: 30) |
| TDLQEDGRNDMSPFSGDGQPFKD | (SEQ ID NO: 31) |
| TDLQERGDNDMSPFGDGSQPFKD | (SEQ ID NO: 32) |
| TDLQEDGRNDMSPFGDGSQPFKD | (SEQ ID NO: 33) |
| PDLLVRGDNDVPPFSGDGQHFMH | (SEQ ID NO: 34) |
| PDLLVDGRNDVPPFSGDGQHFMH | (SEQ ID NO: 35) |
| PDLLVRGDNDVPPFGDGSQHFMH | (SEQ ID NO: 36) |
| PDLLVDGRNDVPPFGDGSQHFMH | (SEQ ID NO: 37) |
| PDLQERGDNDISPFSGDGQPFKD | (SEQ ID NO: 38) |
| PDLQEDGRNDISPFSGDGQPFKD | (SEQ ID NO: 39) |
| PDLQERGDNDISPFGDGSQPFKD | (SEQ ID NO: 40) |
| PDLQEDGRNDISPFGDGSQPFKD | (SEQ ID NO: 41) |

All of these sequence except for SEQ ID NO's:17-20 and 34-37 are the examples of the peptides of the invention which comprise the general amino acid sequence of DLQEXXX-NDXSPFXXXXQPF (SEQ ID NO:2). This general amino acid sequence represents the common sequence of the corresponding sequence to AC-100 in relatively evolved mammalian species such as human, chimpanzee, macaque, and canine, all of which show relatively higher homology each other as compared to the homology to rodent orthologues.

Further, SEQ ID NO's:21-33 are the examples of the peptides of the invention which comprise the general amino acid sequence of TDLQEXXXNDXSPFXXXXQPFKD (SEQ ID NO:3).

The peptide of SEQ ID NO:21 above was presented in U.S. Pat. No. 6,911,425 as one of the peptides comprising a few characteristic motifs such as an RGD integrin-binding motif (SEQ ID NO:42), an SGDG glycosaminoglycan-binding motif (SEQ ID NO:43), and a calcium-binding motif, DXDXSXFXGXXQ (SEQ ID NO:44), having hard tissue formation activities in the bone or teeth.

However, as presented in this invention, it was found that none of these characteristic motifs in their exact sequence and position is necessary for the hard tissue formation activities. An alternative common amino acid sequence motif of DLXXXXXNDXXPFXXXXQXF (SEQ ID NO:1) is shown here to be essential for such activities.

When both or either of RGD and/or SGDG motifs of the peptide of SEQ ID NO: 21, which is also known as AC-100, were/was scrambled to DGR and GDGS, respectively, none of them lost its activities to stimulate bone formation. See EXAMPLE 2. Although Hayashibara, et. al. previously reported in Journal of Bone and Mineral Research 19(3):455-462, 2004 that scrambling the RGD or SGDG sequence diminished the bone formation activities of AC-100, only a very low doses of the scrambled peptides were tested in the reported experiments and no further investigations have been pursued since then. In the experiments for this invention, optimal doses were used.

In addition, when RGD was scrambled to DGR, it automatically destroyed the calcium-binding motif of DXDX-SXFXGXXQ by changing the first "D" of the motif to "R." However, the peptide did not lose the bone formation activities.

These results suggested that although the peptide of SEQ ID NO:21, or AC-100, is active in hard tissue formation, that the essential amino acid sequence motif for the activity was not RGD, SGDG, or DXDXSXFXGXXQ.

A chimpanzee orthologue of AC-100 was recently identified and turned out its amino acid sequence did not contain RGD but was rather RWD (SEQ ID NO:28). This also shows that an RGD integrin binding motif is not essential for the bone growth activities with AC-100.

AC-100 sequence was originally derived from a partial sequence of human MEPE. In a recent structural analysis of MEPE produced by mammalian cells, it was discovered that a chondroitin sulfate chain with molecular weight of about 22 to 30 kDa was bound to the "S" in the SGDG glycosaminoglycan binding-motif (Grimm, et. al., Protein Society, Boston, Jul. 21-25, 2007). This suggests that the SGDG sequence is masked by a large carbohydrate chain in the MEPE molecule and therefore that it is unlikely that the SGDG sequence itself has any specific biological role in the original native MEPE molecule. Thus, it is reasonable to speculate that scrambling the SGDG sequence in AC-100 might not affect the overall biological functions of AC-100 peptide.

Several amino acid sequence motifs were synthesized and tested for their bone formation activities in a human mesenchymal stem cell assay and a rat calvarial defect model. Combining the results from these experiments and the sequence analyses of the corresponding sequence of AC-100 in a few other orthologues of MEPE, such as macaque (SEQ ID NO:30), rat/mice (SEQ ID NO:34), and canine (SEQ ID NO:38), it was concluded that the essential amino acid sequence motif for the bone formation activities is DLXXXXXNDXXPFXXXXQXF (SEQ ID NO:1).

Further to these results, several larger amino acid sequence motifs than the SEQ ID NO: 1 were synthesized and tested for hard tissue formation activities.

As a result, several peptides sharing the same amino acid sequence motif of TDLQEXXXNDXSPFXXXXQPFKD (SEQ ID NO:3) demonstrated potent activities on hard tissue formation activities. The peptide of SEQ ID NO:21, or AC-100, which also has this amino acid sequence motif, has shown a dose-dependent cartilage formation activities in the knee joint of a goat osteoarthritis model as indicated in EXAMPLE 3 and EXAMPLE 4 of the present invention.

As described above, there are very few efficacious therapies that regenerate new cartilage in the degenerated joints. While bones are highly vascularized, cartilage is less vascularized. This makes delivery of systemically administered drug to cartilage very difficult. More importantly, it significantly decreases the availability of the cells that can be differentiated into cartilage cells (chondrocytes) and repair cartilage.

EXAMPLE 3 is an implantation study with a goat OA model in which the cartilage defect was deep enough to reach the subchondral bone. From the beginning of the treatment process, the cartilage defect was exposed to the subchondral bone. Because subchondral bone includes many mesenchymal stem cells, such cells could be stimulated by AC-100 that was contained in the collagen scaffold directly implanted in the defect. It was surprising that, as exhibited in FIGS. 3 and 4, respectively, AC-100 treated groups showed dose dependent regeneration of cartilage that was histologically verified. In the standard therapy for a deep osteochondral defect with an implantable scaffold like this model, a typical response is formation of fibrocartilage, which consists of a mixture of white fibrous tissue and cartilaginous tissue in various proportions and as such is not purely cartilage.

In less severe cases of OA where the cartilage defect is not deep enough to reach the subchondral bones, the number of available cells that could repair cartilage is limited because cartilage is not vascularized. The only possible source of cells is the vascularization in the synovial membrane.

Arthroscopic surgical techniques were developed to increase the availability of the cells for such OA cases. As described above, arthoscopic techniques such as drilling and microfractures involve drilling holes (2-2.5 mm or 0.5-1 mm respectively) through the cartilage into the subchondral bone. Exposure of the subchondral bone and contact with mesenchymal stem cells results in filling of the defects with either fibrocartilage (large holes) or a mix of hyaline and fibrocartilage (smaller holes) (Steadman et al., Oper Technol Orthop 1997; 7:300).

The experiments in EXAMPLE 4 involved a combination therapy of the microfracture methodology and intra-articular injection of AC-100. In this model, intra-articularly injected AC-100 was thought to stimulate the cells recruited from the subchondral bone through the holes made by the microfracture surgery. As exhibited on the left side halves of FIGS. 5 and 6, respectively, AC-100 dose dependently increased new cartilage formation in the defects in this experiment. The saline group in this experiment represents the microfracture therapy currently employed as one of the standard therapies for OA treatments.

EXAMPLE 4 also involved intra-articular injection of AC-100 without microfracture surgery. In this model, cartilage defects did not reach the subchondral bone and no microfracture hole was made. Thus, there was no cell supply from the subchondral bone. The only possible source of cells for cartilage repair were those that initially existed in the synovial fluid and those which could be supplied from blood vessels in the synovial membrane. These sole sources of cells constituted a small number.

Surprisingly, however, intra-articularly injected AC-100 in this non-microfracture OA model dose-dependently increased new cartilage formation in the defects as shown on the right side of FIG. 5 and FIG. 6, respectively.

A further unexpected result was that two particularly high dose groups of AC-100 (25 mg and 125 mg, respectively) indicated more cartilage formation than the saline group of the microfracture experiment (compare both sides of FIGS. 5 and 6, respectively). As described above, microfracture surgery without other treatments is the current standard therapy. It is widely believed that recruiting of repair cells from the subchondral bone through the holes assists cartilage repair. Nonetheless, simple intra-articular injections of AC-100 into a synovial space that is believed to have very limited cell supply seemed a better treatment for cartilage repair as compared to the cell recruitment methodology.

A majority of OA patients may be categorized in a non-severe group where in cartilage defects do not reach the subchondral bone. Most of them are currently treated with anti-inflammatory agents, analgesics, intra-articular HA infusions, and so forth expecting delaying the advancement of the disease. The results from EXAMPLE 4 suggest that minimal intra-articular injection of AC-100 could not only delay disease advancement but also heal the degenerated cartilage.

Sequences

All or any of the amino acids in the above sequences may be in the D- or L-conformation and may be substituted with equivalent analogs. The preferred embodiments comprise naturally occurring amino acids in the L-conformation.

All or any of the above sequences may be amidated, non-amidated, or otherwise modified on their C-terminus, or carboxylated, non-carboxylated, or otherwise modified on their N-terminus.

In addition, multimers of any of the foregoing peptides are provided. Multimers include dimers, trimers, tetramers, pentamers, hexamers, etc. Thus, a peptide of the invention having a length of from about 20 to about 50 amino acids can be multimerized, optionally with an intervening linker, such that a subject peptide occurs in tandem arrays of two, three, four, five, six, or more copies. Furthermore, two or more different peptides of the invention can be multimerized with one another, forming "heteromultimers." Thus, e.g., a multimer may comprise a first and a second peptide, linked together by peptide bonds, optionally with a linker molecule such as one to ten glycine residues.

Peptidic compounds of the invention can be obtained using any known method, including, e.g., solid phase peptide synthesis techniques, where such techniques are known to those of skill in the art. Methods for synthesizing peptides are well known in the art and have been amply described in numerous publications, including, e.g., "The Practice of Peptide Synthesis" M. Bodanszky and A. Bodanszky, eds. (1994) Springer-Verlag; and Jones, The Chemical Synthesis of Peptides (Clarendon Press, Oxford)(1994). Generally, in such methods a peptide is produced through the sequential additional of activated monomeric units to a solid phase bound growing peptide chain. Also of interest is the use of submonomers in solid phase synthesis, as described in WO 94/06451, the disclosure of which is herein incorporated by reference.

Instead of solid phase synthesis, the subject peptidic compounds of the subject invention may be prepared through expression of an expression system comprising a polynucleotide encoding the peptidic compound. Any convenient methodology may be employed, where methodologies that may be employed typically include preparation of a nucleic acid molecule comprising a nucleotide sequence encoding the subject peptide, introduction of the encoding region into a vector for expression, transformation of a host cell with the vector, and expression and recovery of the product. Protocols for accomplishing each of the above steps are well known in art. See Sambrook, Fritsch & Maniatis, Molecular Cloning, A Laboratory Manual (Cold Spring Harbor Press, Inc.)(1989).

Therapeutic Methods

The present invention also discloses a method for promoting cartilage formation by administering a therapeutically effective amount of a peptidic compound having a common amino acid sequence motif of SEQ ID NO: 1, which includes the peptide having an amino acid sequence of SEQ ID NO: 21, or AC-100. The methods of the present invention may be used to treat or prevent diseases and conditions which involve pathological or traumatic reduction or defects of cartilage in a mammal body by administering an effective amount of the peptidic compound alone or in combination with a carrier material.

Examples of conditions and diseases amenable to treatment according to the method of the invention include any condition associated with a defect in cartilage that has been caused by a pathological condition such as rheumatoid arthritis or by a traumatic condition such as osteoarthritis.

Rheumatoid arthritis is an autoimmune disease which the self immune system attacks and destroys the self tissues, in particular, the cartilages in the joints all over the body. In such a condition, joints of the patients are damaged by inflammation and the cartilage in the joints is often destroyed, both of which cause significant pain. Several treatments are available to date to control such autoimmune reactions but there is very little treatment to regenerate the cartilage tissues that smooth the movement of the joints such as bending and stretching without pain. Rapid reconstruction of the lost cartilage by the disease would help the patients significantly.

An aspect of the method of treatment of the invention may include a treatment of a disease such as rheumatoid arthritis or osteoarthritis by administering a formulation of the invention. The method may include determining an area of a subject which is prone to disease and administering the formulation locally to the area of disease. The method may further include not only diagnosing the patient and localizing the area of disease but testing the area to determine the level of disease such as the degree of bending of a joint which can be carried out and thereafter administering the formulation, allowing the formulation to act on the area and thereafter retesting the patient to determine the level of improvement in the area such as improvement in the degree of bending of a joint. Those skilled in the art reading this disclosure will understand that other tests of the patient based on other diseases can be carried out and that after performing those tests a formulation of the invention can be administered followed by a period of time where the formulation is allowed the act and then followed by retesting the subject to determine the level of improvement. In any of the methods the various methods of administration disclosed here can be utilized. A particular method involves implanting a sponge comprised of collagen having a therapeutically effective amount of a peptide as taught herein absorbed onto the sponge. Another particular method is intra-articular injection of a therapeutically effective amount of a peptide following a microfracture surgery as taught herein. The same intra-articular injection can be also used in the treatment process which does not involve microfracture surgery.

Osteoarthritis is similar to rheumatoid arthritis in that the cartilage in the joints is lost that typically causes a significant pain when moving the affected joints. This condition, however, is not by pathological events but by a mechanical stress on the joints. Thus, this condition tends to happen in the joints which bear a large mechanical burden and the most common joint affected by this is a knee. Although this condition is more common with the aged, it also often happens in young athletes. In those, depending upon their area of athletic specialty, this condition happens other joints than the knees such as elbows, shoulders, etc. Rapid reconstruction of the lost cartilage in such joints would help the patients significantly.

As used herein, an "effective amount" or "therapeutically effective amount" are used interchangeably and refer to amount of the peptidic compound for use with the subject methods is an amount that enhances cartilage formation is a measurable amount and may be by at least about 10%, at least about 15%, at least about 20%, at least about 25%, at least about 30%, at least about 35%, at least about 40%, at least about 45%, at least about 50%, at least about 55%, or at least about 60%, or more, when compared to a suitable control. Suitable controls are, in the case of experimental animals, an animal not treated with the peptide, e.g., treated with vehicle, or treated with an irrelevant peptide; and in the case of human subjects, a human subject treated with a placebo, or a human subject before treatment with a peptide of the invention.

In some embodiments, an effective amount of peptidic compound for use with the subject methods is an amount that accelerates cartilage formation, by a measurable amount which may be at least about 10%, at least about 15%, at least about 20%, at least about 25%, at least about 30%, at least about 35%, at least about 40%, at least about 45%, at least about 50%, at least about 55%, or at least about 60%, or more, when compared to a suitable control.

In other embodiments, an effective amount of peptidic compound is an amount that accelerates the healing speed of the individual suffering from the arthritis or any other damaged cartilage conditions. For example, in these embodiments, an effective amount of the peptidic compound is an amount effective to accelerate the healing of the arthritic conditions involving cartilage regeneration by a measurable amount which may be at least about 10%, at least about 15%, at least about 20%, or at least about 25%, or more, compared to the expected speed of healing without administration of said peptidic compound.

Routes of Administration

Formulations of peptidic compound for use with the subject methods are administered to an individual using any available method and route suitable for drug delivery, including in vivo and ex vivo methods, as well as systemic and localized routes of administration.

Conventional and pharmaceutically acceptable routes of administration include intranasal, intrapulmonary, intramuscular, intratracheal, subcutaneous, intradermal, intra-articular, topical application, intravenous, rectal, nasal, oral and other parenteral routes of administration. Routes of administration may be combined, if desired, or adjusted depending upon the immunomodulatory nucleic acid molecule and/or the desired effect on the immune response. The peptidic compound formulations for use with the methods of the present invention can be administered in a single dose or in multiple doses.

The peptidic compound formulations can be administered to a subject using any available conventional methods and routes suitable for delivery of conventional drugs, including systemic or localized routes. In general, routes of administration contemplated by the invention include, but are not necessarily limited to, enteral, parenteral, implantable, or inhalational routes.

Parenteral routes of administration other than inhalation administration include, but are not necessarily limited to, topical, transdermal, subcutaneous, intramuscular, intraorbital, intracapsular, intraspinal, intrasternal, intra-articular, and intravenous routes, i.e., any route of administration other than through the alimentary canal. Parenteral administration can be carried to effect systemic or local delivery of peptides of the invention. Where systemic delivery is desired, administration typically involves invasive or systemically absorbed topical or mucosal administration of pharmaceutical preparations.

The peptidic compound formulations of the invention can also be delivered to the subject by enteral administration. Enteral routes of administration include, but are not necessarily limited to, oral and rectal (e.g., using a suppository) delivery.

Methods of administration of the peptidic compound formulation through the skin or mucosa include, but are not necessarily limited to, topical application of a suitable pharmaceutical preparation with or without a permeation enhancer, transdermal transmission, injection and epidermal administration. Also contemplated for delivery of the peptidic compound formulation of the invention is a patch containing therein a peptide of the invention. A patch can be applied to the skin, or to other tissue, e.g., gum tissue. Any known patch delivery system that is suitable for oral delivery system can be used. See, e.g., U.S. Pat. No. 6,146,655.

The peptidic compound of this invention can be formulated with a carrier material which can contain the peptidic compound. Such carrier materials can be injectable or implantable depending upon the needs of the patients. As an example, the peptic compound can be formulated with a collagen carrier as indicated in EXAMPLE 3 and surgically implanted directly into the cartilage defects in the affected joint. In this method of treatment, the carrier can be a biodegradable carrier that enables a sustained release of the peptidic compound of this invention, in which case the affected area in the cartilage can be exposed to the therapeutic peptide compound of this invention longer that could increase the benefit of the treatment.

In another embodiment, the peptidic compound of this invention can be formulated with a carrier material which can contain the peptidic compound and can be administered directly into the intra-articular space such as joints. For instance, if the peptidic compound of this invention is formulated with hyarulonic acid that is widely used to treat the arthritic condition simply to smoothen the movement of the joint, the formulation can be directly injected into the intra-articular space.

The peptidic compound of this invention can be also formulated with tiny particles of biodegradable carrier materials that can be suspended in an injectable solution and directly injected into the intra-articular space. This would also enable a sustained release of the peptide compound of this invention to extend its efficacy on cartilage formation.

Peptidic compound formulations of the present invention can also be delivered to an individual by administering to the individual a nucleic acid molecule comprising a nucleotide sequence that encodes the peptide of the invention. The terms "polynucleotide" and "nucleic acid molecule" are used interchangeably herein to refer to polymeric forms of nucleotides of any length. The polynucleotides may contain deoxyribonucleotides, ribonucleotides, and/or their analogs. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a gene encoding the subject peptides or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Vectors include, but are not limited to, plasmids; cosmids; viral vectors; artificial chromosomes (YAC's, BAC's, etc.); mini-chromosomes; and the like. Vectors are amply described in numerous publications well known to those in the art, including, e.g., Short Protocols in Molecular Biology, (1999) F. Ausubel, et al., eds., Wiley & Sons.

Expression vectors may be used to introduce a nucleic acid molecule encoding the AC-100 peptide into a cell of an individual. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

An expression vector comprising a nucleotide sequence encoding the peptidic compound of the invention may be introduced into tissues or host cells by any number of routes, including viral infection, microinjection, or fusion of vesicles. Jet injection may also be used for intramuscular administration, as described by Furth et al. (1992), *Anal Biochem* 205:365-368. The expression vector may be coated onto gold microparticles, and delivered intradermally by a particle bombardment device, or "gene gun" as described in the literature (see, for example, Tang et al. (1992), *Nature* 356:152-154), where gold microprojectiles are coated with the expression vector, then bombarded into skin cells.

Dosages

Although the dosage used will vary depending on the clinical goals to be achieved, a suitable dosage range is one which provides up to about 1 μg, to about 1,000 μg, to about 10,000 μg, to about 25,000 μg, to about 50,000 μg, or to about 100,000 μg of the formulation of a peptide of SEQ ID NO:1, such as AC-100, used with the subject methods of the present invention. The formulations of the invention can be administered in a single dosage or several smaller dosages over time. Alternatively, a target dosage of a peptide can be considered to be about 0.1-1000 μM, about 1-500 μM, or about 5-250 μM in a sample of host blood drawn within the first 24-48 hours after administration of the peptide. In one embodiment the formulation is administered one time and not administered again.

The effect on cartilage formation may be dose-dependent. Therefore, to increase potency by a magnitude of two, each single dose is doubled in concentration. Increased dosages may be needed to achieve the desired therapeutic goal. The invention thus contemplates the administration of multiple doses to promote cartilage formation. When multiple doses are administered, subsequent doses are administered within about 16 weeks, about 12 weeks, about 8 weeks, about 6 weeks, about 4 weeks, about 2 weeks, about 1 week, about 5 days, about 72 hours, about 48 hours, about 24 hours, about 12 hours, about 8 hours, about 4 hours, or about 2 hours or less of the previous dose.

In view of the teaching provided by this disclosure, those of ordinary skill in the clinical arts reading this disclosure will be familiar with, or can readily ascertain, suitable parameters for administration of peptides according to the invention.

Combination Therapy

In some embodiments, a subject method of treating diseases or conditions that involve cartilage formation or regeneration comprises administering the peptidic compound in an individual and at least a second therapeutic agent. Factors that control inflammation or pain, such as ibuprofen or steroids, can be part of the pharmaceutical composition to reduce swelling and inflammation associated with the disease or condition involving angiogenesis.

Additional therapeutic agents that are suitable for use in a subject combination therapy include, but are not limited to anti-inflammatory agents or analgesics.

Antiinflammatory Agents

Suitable anti-inflammatory agents include, but are not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone, glucocorticoidspropionic acid derivatives, alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, tioxaprofen, indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, zomepirac, flufenamic acid, meclofenamic acid, mefenamic acid, niflumic acid, olfenamic acid, diflunisal, ufenisal, isoxicam, piroxicam, sudoxicam, tenoxican, acetyl salicylic acid, sulfasalazine, apazone, bezpiperylon, feprazone, mofebutazone, oxyphenbutazone, phenylbutazone, celecoxib and rofecoxib Formulations In general, the peptidic compound formulations are prepared in a pharmaceutically acceptable composition for delivery to a host. Pharmaceutically acceptable carriers preferred for use with the peptides of the invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising a peptide of the invention may also be lyophilized using means well known in the art, for subsequent reconstitution and use according to the invention. Also of interest are formulations for liposomal delivery and formulations comprising microencapsulated peptides.

In general, the pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. Preservatives and other additives may also be present such as, for example, antimicrobials, antioxidants, chelating agents, and inert gases and the like.

Absorption promoters, detergents and chemical irritants (e.g., keratinolytic agents) can enhance transmission of the peptidic formulation into a target tissue (e.g., through the skin). For general principles regarding absorption promoters and detergents which have been used with success in mucosal delivery of organic and peptide-based drugs, see, e.g., Chien, *Novel Drug Delivery Systems*, Ch. 4 (Marcel Dekker, 1992). Examples of suitable nasal absorption promoters in particular are set forth at Chien, supra at Ch. 5, Tables 2 and 3; milder agents are preferred. Suitable agents for use in the method of this invention for mucosal/nasal delivery are also described in Chang, et al., *Nasal Drug Delivery*, "Treatise on Controlled Drug Delivery", Ch. 9 and Tables 3-4B thereof, (Marcel Dekker, 1992). Suitable agents which are known to enhance absorption of drugs through skin are described in Sloan, Use of Solubility Parameters from Regular Solution Theory to Describe Partitioning-Driven Processes, Ch. 5, "Prodrugs: Topical and Ocular Drug Delivery" (Marcel Dekker, 1992), and at places elsewhere in the text. All of these references are incorporated herein for the sole purpose of illustrating the level of knowledge and skill in the art concerning drug delivery techniques.

A colloidal dispersion system may be used for targeted delivery of the peptidic compound to specific tissue. Colloidal dispersion systems include macromolecule complexes, nanocapsules, microspheres, beads, and lipid-based systems including oil-in-water emulsions, micelles, mixed micelles, and liposomes.

Liposomes are artificial membrane vesicles which are useful as delivery vehicles in vitro and in vivo. It has been shown that large unilamellar vesicles (LUV), which range in size from 0.2-4.0 Fm can encapsulate a substantial percentage of an aqueous buffer comprising large macromolecules. RNA and DNA can be encapsulated within the aqueous interior and be delivered to cells in a biologically active form (Fraley, et al., (1981) *Trends Biochem. Sci.*, 6:77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidyl-ethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine. Exemplary liposome/therapeutic nucleic acid compositions suitable for use in a subject method are described in Louria-Hayon et al. (2002) *Vaccine* 20:3342.

Where desired, targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various well known linking groups can be used for joining the lipid chains to the targeting ligand (see, e.g., Yanagawa, et al., (1988) *Nuc. Acids Symp. Ser.,* 19:189; Grabarek, et al., (1990) *Anal. Biochem.,* 185:131; Staros, et al., (1986) *Anal. Biochem.* 156:220 and Boujrad, et al., (1993) *Proc. Natl. Acad. Sci. USA,* 90:5728). Targeted delivery of a therapeutic peptidic formulation can also be achieved by conjugation of the therapeutic formulation to a surface of viral and non-viral recombinant expression vectors, to an antigen or other ligand, to a monoclonal antibody or to any molecule which has the desired binding specificity.

Induction of Cartilage Formation In Vivo

In order to accomplish stimulation of cartilage formation in vivo (e.g., as in the context of therapeutic cartilage formation), a peptidic compound formulation can be administered in any suitable manner, preferably with pharmaceutically acceptable carriers. One skilled in the art will readily appreciate that the a variety of suitable methods of administering a formulation comprising a peptidic compound of this invention in the context of the present invention to a subject are available, and, although more than one route can be used to administer a particular compound, a particular route can provide a more immediate, more effective, and/or associated with fewer side effects than another route. In general, a peptidic compound formulation can be administered according to the method of the invention by, for example, a parenteral, subcutaneous, intravenous, intra-arterial, inter-pericardial, intramuscular, intraperitoneal, intra-articular, transdermal, transcutaneous, subdermal, intradermal, or intrapulmonary route.

The peptidic compound may be administered locally for example, direct injection (e.g., intra-articular or subcutaneous injection) at or near the desired treatment site, by introduction of the peptide subcutaneously at a site near a desired treatment site (e.g., subcutaneous injection in a joint which cartilage regeneration is desired), by intra-articular injection, by introduction (e.g., by implantation directly into the affected cartilage) of a peptidic formulation in a biocompatible gel or capsule within or adjacent a treatment site, by injection directly into the intra-articular space or other tissue in which increased cartilage formation is desired, etc.

In another embodiment of interest, the peptidic formulation is delivered in the form of a biocompatible gel, which can be implanted (e.g., by injection into or adjacent a treatment site, by extrusion into or adjacent a tissue to be treated, etc.).

Gel formulations comprising the peptidic formulation can be designed to facilitate local release for a sustained period (e.g., over a period of hours, days, weeks, etc.). The gel can be injected into or near a treatment site, e.g., using a needle or other delivery device. In one embodiment, the gel is placed into or on an instrument which is inserted into the tissue and then slowly withdrawn to leave a track of gel, resulting in stimulation of cartilage formation along the path made by the instrument.

In other embodiments it may be desirable to deliver the formulation topically, e.g., for localized delivery, e.g., to facilitate wound healing that needs to be associated with cartilage formation, e.g., re-construction of ears. Topical application can be accomplished by use of a biocompatible gel, which may be provided in the form of a patch, or by use of a cream, foam, and the like. Several gels, patches, creams, foams, and the like appropriate for application to wounds can be modified for delivery of formulations according to the invention (see, e.g., U.S. Pat. Nos. 5,853,749; 5,844,013; 5,804,213; 5,770,229; and the like). In general, topical administration is accomplished using a carrier such as a hydrophilic colloid or other material that provides a moist environment.

In other embodiments, the formulation is delivered locally or systemically, preferably locally, using a transdermal patch. Several transdermal patches are well known in the art for systemic delivery of nicotine to facilitate smoking cessation, and such patches may be modified to provide for delivery of an amount of the peptidic compound effective to stimulate cartilage formation according to the invention.

In other methods of delivery, the formulation can be administered using iontophoretic techniques. Methods and compositions for use in iontophoresis are well known in the art (see, e.g., U.S. Pat. Nos. 5,415,629; 5,899,876; 5,807,306; and the like).

The formulation of the present invention can be administered with any other known agent, e.g. anti-inflammatory agent. A peptide of the invention can be administered simultaneously with (e.g., in admixture with, or in separate formulations) within about 15 minutes, about 30 minutes, about 60 minutes, about 2 hours, about 5 hours, about 10 hours, about 12 hours, about 24 hours, about 36 hours, about 4 days, about 7 days, or more, of another agent. In a particular embodiment the peptide is administered one time and not administered again.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Synthesis of the Peptides of the Present Invention

Several different peptides were synthesized by the t-Boc strategy and prepared in the C-terminal amide form. These peptides are as follows:

```
TDLQERGDNDISPFSGDGQPFKD      (SEQ ID NO: 21)

TDLQEDGRNDISPFSGDGQPFKD      (SEQ ID NO: 22)

TDLQERGDNDISPFGDGSQPFKD      (SEQ ID NO: 23)

TDLQEDGRNDISPFGDGSQPFKD      (SEQ ID NO: 24)

PDLLVRGDNDVPPFSGDGQHFMH      (SEQ ID NO: 34)
(C-terminus amidated)
```

The peptide of SEQ ID NO:21 is also referred to here as AC-100 or Dentonin®.

Amino acid derivatives and resins were purchased from a commercial source and synthesized by standard solid-phase t-Boc chemistry starting with benzhydrylamine resin. Synthesis is performed at room temperature. Trifluoroacetic acid (65%) in dichloromethane (DCM) is used to remove the butyloxycarbonyl (Boc) protecting group during the synthesis. All amino acids are coupled using diisopropylcarbodiimide (DIC) or DIC and hydroxybenzotriazole (HOBt) as the activating agent.

The peptide is cleaved from the resin using the standard hydrogen fluoride (HF) technique. Anisole is used as a scavenger to minimize side reactions. The reaction is carried out at −8 to −5° C. HF concomitantly removes the benzyl protecting group of the side chain of the Ser, Asp, Lys, Arg, Glu, and Thr residues while cleaving the peptide from the resin. Use of the benzhydrylamine resin yields a polypeptide with an amidated C-terminus after cleavage ($CONH_2$ rather than COOH). The crude peptide is extracted using acetic acid and lyophilized to dryness.

Purification is achieved on $C_{18}$ resin by reverse phase high performance liquid chromatography (RP-HPLC) in Triethylammonium acetate/water at pH 5.5 and developed with an Acetonitrile gradient. The TEAA salt of the peptide is converted to the acetate salt by ion exchange using the same preparative column from the previous step equilibrated in 0.2% Acetic acid in water and the peptide is then eluted with an Acetonitrile gradient. Based on in-process analytical RP-HPLC purity checks, fractions that are ≧95% pure are pooled, distributed in 1200 mL lyophilization flasks, flash frozen, and lyophilized to dryness.

Example 2

The peptide of SEQ ID NO:34 was tested in a proliferation assay with human mesenchymal stem cells (hMSC), which AC-100 has demonstrated similar levels of activities as compared to Bone Morphogenetic Protein-2 (BMP-2) and Insulin-like Growth Factor-1 (IGF-1), (Nigel, et. al., Journal of Cellular Biochemistry 93 (6): 1107-1114, 2004). The same protocol and positive controls were used in this experiment.

SEQ ID NO:34 was selected for this experiment since the amino acid sequence of this peptide was derived from the corresponding region in rat and mouse MEPE where AC-100 was derived from human MEPE. Furthermore, as compared to all other known mammalian corresponding regions to AC-100, it is the least homologous to AC-100 (the human sequence).

Significant proliferation activities of the hMSC by tritiated-thymidine incorporation as compared to the vehicle were demonstrated by the peptide of SEQ ID NO:34, BMP-2, and IGF-1. The degree of activities was very similar among these three materials.

From the results, it was concluded that the peptides which share the common amino acid sequences of DLXXRGDNDXXPFSGDGQXF (SEQ ID NO:45) had hard tissue formation activities at the equivalent levels to those of AC-100.

As a next step, necessity of RGD integrin-binding motif (SEQ ID NO:42) and SGDG glycosaminoglycan attachment motif (SEQ ID NO:43) to the bone formation activities was examined by testing the selected peptides synthesized in EXAMPLE 1 in a rat calvaria defect model. In this model an 8 mm diameter defect is created in the rat parietal bones and a collagen sponge cut to size is inserted into the defect. The test article is soaked into the sponge. Sub-cutaneous injections are administered daily for 6 days post-surgery. After 28 days post-surgery the rats are euthanized and the calvariae collected. The degree of bone bridging was determined by histology analysis using a qualitative scoring system. The tested peptides were SEQ ID NO: 22, 23, and 24, which were also encoded as AC-101, AC-102, and AC-103, respectively.

AC-100 that includes both the RGD integrin-binding motif and the SGDG glycosaminoglycan attachment motif was used as a positive control at the optimal dose.

Figure 1:
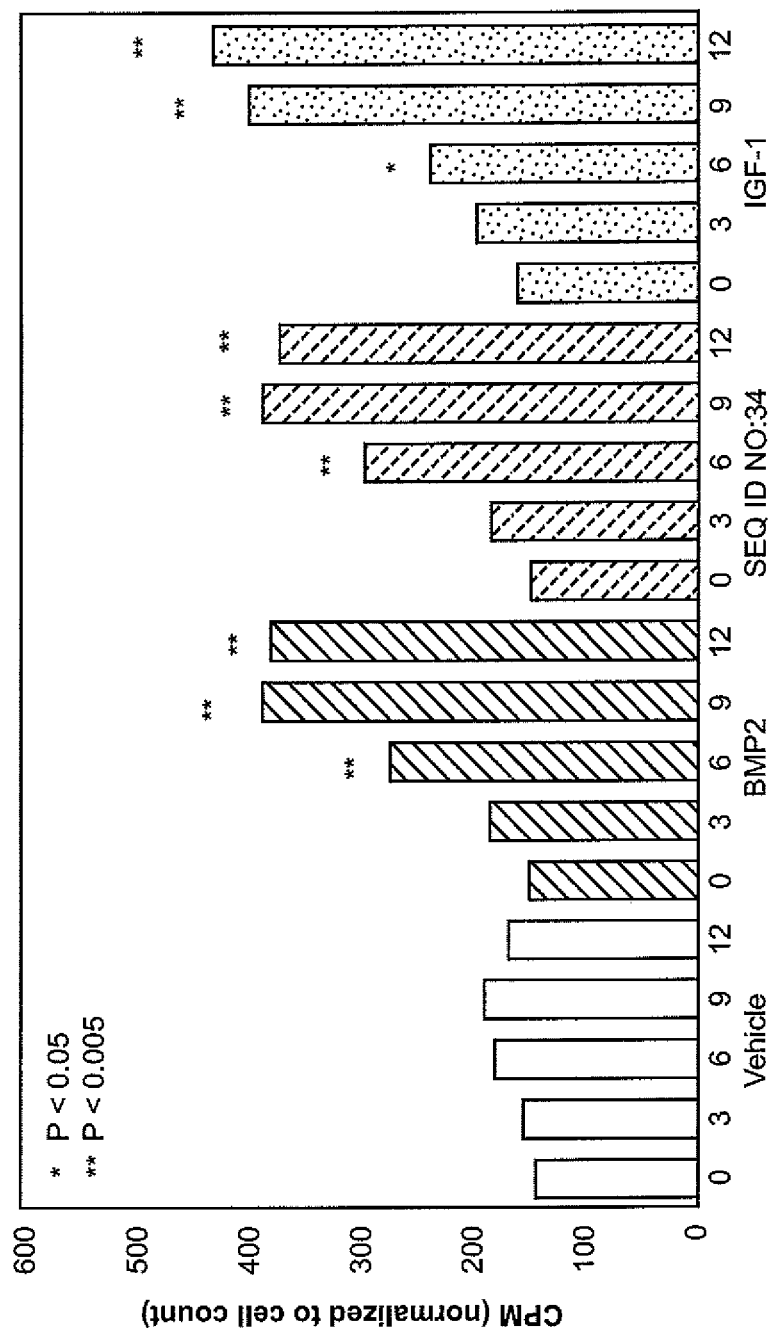
FIG. 1 is a bar graph that exhibits proliferation activities of a few experimental materials on human mesenchymal stem cells (hMSC) by tritiated thymidine incorporation. The peptide of SEQ ID NO:34 was tested for its proliferation activity on human mesenchymal stem cells as compared to CMP-2 and IGF-1.
Figure 2:
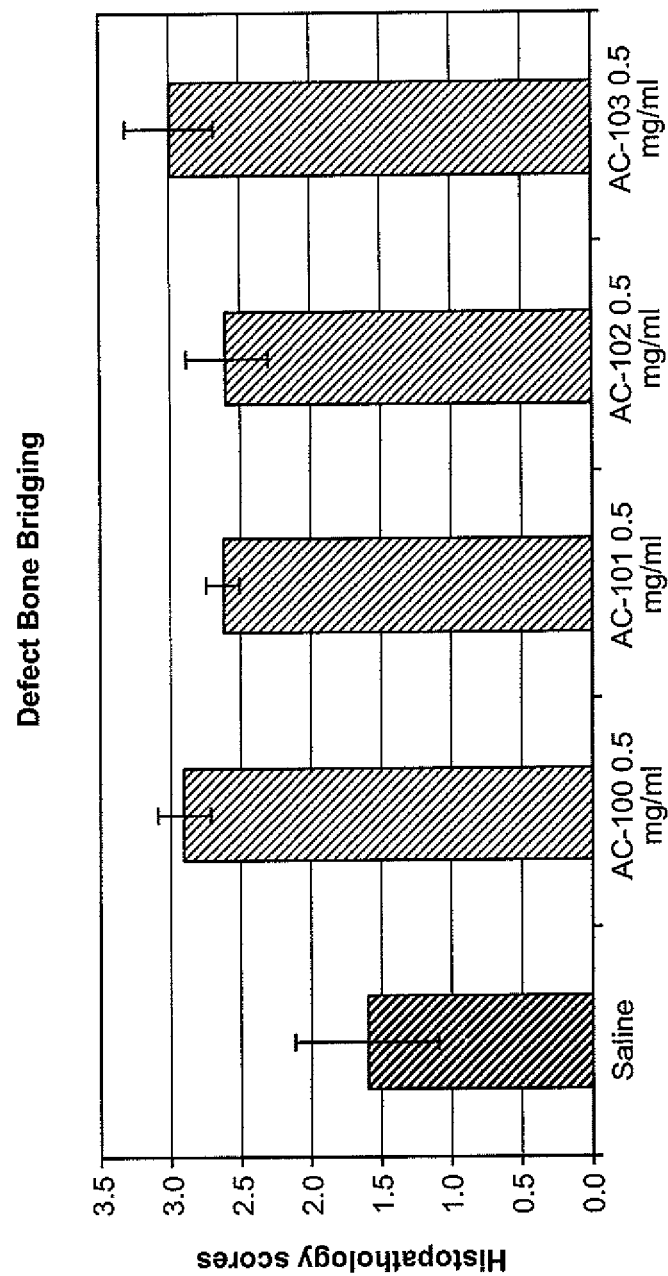
FIG. 2 is a bar graph that demonstrates bone formation activities by bridging of rat calvaria defects by some experimental materials. AC-101, 102, and 103 were tested for their defect bridging activities as compared to AC-100.

The degree of bone bridging induced by AC-101, AC-102 and AC-103 treatment was improved versus saline treatment alone and was comparable to the activity of AC-100 as shown in FIG. 2.

Combining these results, it was concluded that neither the RGD nor the SGDG motif is necessary for the hard tissue formation activities of AC-100 and that the peptides which share the common amino acid sequences of DLXXXXX-NDXXPFXXXXQXF (SEQ ID NO:1) had hard tissue formation activities at the equivalent levels of those of AC-100.

Example 3

Introduction

Normal articular cartilage functions to absorb shock, to bear load and to provide articulating surfaces for diarthrodial joints. The composition of articular cartilage varies with anatomical location on the joint surface, with age and with depth from the surface (Lipshitz H, Etheredge R 3d and Glimcher M J. In vitro wear of articular cartilage. J Bone Joint Surg [AM], 1975 June, 57:4, 527-34). Articular cartilage differs from other musculoskeletal tissues in that it does not have the ability to regenerate itself following traumatic or pathologic afflictions. Once disease or trauma affects the health of articular cartilage, an inevitable degenerative process can occur (Convery F R, Akeson W H, and Keown G H. The repair of large osteochondral defects. An experimental study in horses. Clin Orthop, 1972 January, 82: 253-62). During cartilage degeneration, the amount of interstitial water increases, the proteoglycan content decreases, and the aggregation of proteoglycans decreases (McDevitt C A and Muir H. Biochemical changes in the cartilage of the knee in experimental and natural osteoarthritis in the dog. J Bone Joint Surg [Br], 1976 February, 58:1, 94-101). When the proteoglycan content decreases, cartilage becomes softer (Kempson G E, Spivey C J, Swanson S A and Freman M A. Patterns of cartilage stiffness of normal and degenerate human femoral heads. J Biomech, 1971 December, 4:6, 597-609; Jurvelin J, Kiviranta I, Tammi M and Helminen J H. Softening of canine articular cartilage after immobilization of the knee joint. Clin Orthop, 1986 June, 207, 246-52) and more prone to damage. Because adult articular cartilage is avascular and only 5% cellular, healing of this tissue is very difficult to achieve (Bora F W Jr. and Miller G. Joint physiology, cartilage metabolism, and the etiology of osteoarthritis. Hand Clin, 1987 August, 3:3, 325-36).

In this study, the use of two different concentrations (See Table 1) of AC-100 in conjunction with a collagen sponge and a control with just the collagen sponge was implanted to evaluate the efficacy of AC-100 in repair of bone and cartilage (osteochondral) defects. The implants were intended to serve as an osteochondral allograft for cellular and matrix ingrowth. Efficacy to repair cartilage was assessed using gross and histological examination of the repair tissue. The primary objective was to determine whether AC-100 modifies and/or improves the healing of the osteochondral defect as compared to the study control group and the natural progression of historical controls using this model. This report describes the in vivo, gross and histological findings at the 12 and 24 weeks time points.

Test Material

The following information was supplied.

| | |
|---|---|
| Test material name | Saline with collagen sponge |
| Analyses of test article | 200 μl saline (0 μl AC-100) absorbed into the sponge at the time of surgery. 0.5 mL saline injection into operated stifle once per week for 3 weeks. |
| Implant | Approximately 6 mm diameter × 6 mm thick |
| Test material name | 25 mg AC-100 with collagen sponge (HD or high dose of FIGS. 3 and 4) |
| Analyses of test article | 200 μl AC-100, 200 mg/ml absorbed into the sponge at the time of surgery. 0.5 mL injection of AC-100 80 mg/mL (equivalent to 200 μl AC-100, 200 mg/ml) into the operated stifle joint once per week for 3 weeks. |
| Implant | Approximately 6 mm diameter × 6 mm thick |
| Test material name | 2.5 mg AC-100 with collagen sponge (LD or low dose of FIGS. 3 and 4) |
| Analyses of test article | 200 μl AC-100, 20 mg/ml absorbed into the sponge at the time of surgery. 0.5 mL injection of AC-100 8 mg/mL (equivalent to 200 μl AC-100, 20 mg/ml) into the operated stifle joint once per week for 3 weeks. |
| Implant | Approximately 6 mm diameter × 6 mm thick |

CollaPlug® (Integra) was chosen as the collagen sponge to be used in this study.

Administration of Test Material

The collagen sponge was supplied sterile. The sponge was punched out or cut into the size of the defect allowing for approximately 30% shrinkage. The test articles were absorbed into the sponge at the time of surgery prior to implantation into the defect. Any extra material that was not used at the time of the implant surgery was frozen at −20° C. Aliquots of the test article were supplied for the multiple injections.

The contralateral joint from all animals were not operated on and served for baseline normal measurements.

Experimental Procedures

A total of 15 skeletally mature female Spanish goats were used for this study. They were acquired from an approved, USDA source. The goats weighed between 50-80 lbs. at the start of the study.

The goat was chosen because of the large relative stifle joint size, ease of handling and use in other cartilage repair studies (Shahgaldi B F, Amis A A, Healey F W, McDowell J and Bentley G. Repair of cartilage lesions using biological implants. A comparative histological and biomechanical study in goats. J Bone Joint Surg [Br], 1991 January, 73:1, 57-64).

Identification of Animals

A unique number tattoo or ear tag identified each animal.

Grouping of Animals

Animals were assigned to one of the three groups on the basis of a random allocation of identification numbers.

Treatment

The study design is shown below:

TABLE 1

| Group | Right Medial Femoral Condyle Treatment | Number of Subjects | Sacrifice Period |
|---|---|---|---|
| 1A | 200 μl saline + collagen sponge | 2 | 12 weeks |
| 1B | 200 μl saline + collagen sponge | 3 | 24 weeks |
| 2A | AC-100 (25 mg) + collagen sponge | 2 | 12 weeks |
| 2B | AC-100 (25 mg) + collagen sponge | 3 | 24 weeks |
| 3A | AC-100 (2.5 mg) + collagen sponge | 2 | 12 weeks |
| 3B | AC-100 (2.5 mg) + collagen sponge | 3 | 24 weeks |
| Total | | 15 | |

Animals were observed daily for general health throughout the course of the study. If animals indicated any signs of postoperative complications or other signs of disease, pain or stress, appropriate action was taken. At necropsy, euthanasia was conducted in a humane manner according to the guidelines set forth by the AVMA Panel on Euthanasia (JAVMA, March 2000)

The attending veterinarian performed a clinical diagnosis and treatment on the animal if it showed signs of illness. The sponsor was notified of any illness and needed treatment and its effect.

Surgery and Implantation

A single full-thickness chondral defects were created in the right hind leg stifle joint. The lesion site was located in the anterior medial femoral condyle. The basic surgical procedure was identical for all subjects. All surgeries were performed under strict asepsis. Peri-operative antibiotics and pre-anesthetic medication were used at the discretion of the surgeon. Anesthesia was induced with a mixture of ketamine-xylazine and maintained with a gaseous mix of Isoflurane and oxygen.

The collagen sponge scaffold was hand held while a cylindrical plug was cut using a custom 6 mm diameter biopsy punch that provided a 6 mm long implant. A number of sponge scaffolds were prepared in this manner prior to surgery and were covered until lesion site was created and ready for implantation.

The surgical approach consisted of a curved, lateral skin incision made from the distal one-third of the right femur to the level of the tibial plateau. Using this method, the skin was bluntly dissected and retracted to allow a lateral parapatellar approach into the stifle joint. An incision was made parallel to the lateral border of the patella and patellar ligament. This extended from the lateral side of the fascia lata along the cranial border of the biceps femoris and into the lateral fascia of the stifle joint. The biceps femoris and attached lateral fascia were retracted allowing an incision into the joint capsule. The joint was extended and the patella luxated medially exposing the stifle joint. At this point, the fat pad was retracted to allow visualization of the medial femoral condyle.

The point of marking and preparing the medial femoral condyle (MFC) was defined as 15 mm distal to the medial condyle groove junction and aligned with the medial crest of the trochlear groove. A 6 mm biopsy punch was used to slice through the cartilage outer layer and prevent tearing of the cartilage. The typical MFC defect was 6 mm in diameter and 6 mm in depth.

The cartilage defect was copiously flushed with sterile lactated Ringer's solution and blotted prior to application of the scaffold and test article. The prepared collagen sponge scaffold was implanted into the lesion site. A spatula was also used to seat further the sponge scaffold into the lesion site. The test article was then applied into the sponge scaffold filled lesion site per Sponsor's instructions. Depending on the group assigned to the animal, the appropriate test article was drawn up in a micropipette that was used to deliver the test article into the sponge scaffold within the lesion site and allowed to soak in for approximately three minutes.

The remaining portions of the joint were inspected and carefully flushed if necessary prior to closure. The patella was then reduced. This was followed by routine closure of the joint in three or four layers using appropriate suture material and surgical staples. The animals were allowed to recover and resume weight bearing as tolerated.

Postoperative checks were made for any animal displaying signs of postoperative discomfort. Postoperative analgesics were administered to all animals during the immediate postoperative interval. Additionally, they were given if the animals display any signs of distress of discomfort. Further postoperative treatments consisted of three (3) weekly intra-articular injections (one injection per week under anesthesia for 3 weeks) into the operated knee of the appropriate test article for that study group after which the animals were allowed to recover. All treatments were recorded in the appropriate study documentation. The total postoperative time at final evaluation was either 12 weeks for groups 1A, 2A, and 3A or 24 weeks for groups 1B, 2B, and 3B.

Weekly Injections

Each animal received an injection of 0.5 mL of the appropriate test article into the operated knee joint at 1, 2 and 3 weeks post surgery.

Necropsy

Animals were humanely sacrificed at Day 84 (12 weeks) or Day 168 (24 weeks) postoperatively. Bodyweights were recorded immediately prior to sacrifice. Deep anesthesia was induced with a mixture of ketamine-xylazine and the subject exsanguinated according to the guidelines set forth by the AVMA Panel on Euthanasia (JAVMA, March, 2000).

A complete gross necropsy was conducted (see Table 2). Gross evaluation was performed on the heart, liver, lungs, kidneys, spleen, and popliteal lymph nodes for signs of any systemic toxicity from the implant material. Lymph nodes in close proximity to the joint were examined. The articulating surfaces opposing the defect sites were examined for any abnormal joint surface and if necessary stained with India ink to determine fibrillation. Additionally, gross evaluations of the knee joints were made to determine the cartilage repair based on previous scoring criteria listed in Table 3. Femora, tibiae, synovium, and popliteal lymph nodes were harvested and placed into appropriately labeled containers. Immediately following tissue harvest, gross morphological examination of the cartilage surface was done and photographic records made of each specimen.

The stifle joints were initially grossly evaluated. The specimen and contralateral medial femoral condyle were preserved in neutral buffered formalin. Only the operated medial femoral condyle was submitted for histological processing. The contralateral unoperated medial femoral condyle and any other soft tissues were processed.

TABLE 2

Gross Evaluation and Sample Collection

| Sample | Gross Evaluation | Sample Collection | Photograph and Score |
|---|---|---|---|
| Heart | X | | |
| Lungs | X | | |
| Kidneys | X | | |
| Spleen | X | | |
| Popliteal lymph nodes | X | X | |
| Knee joint (includes articulating defect site)[1] | | X | X |

[1] = stained with India ink to determine fibrillation if necessary

After collection of the knee joints, the joints were opened, photographed and the surface of the defect site scored as indicated in Table 3. The synovial membrane was examined for any inflammation.

Gross Morphological Observations

TABLE 3

Scoring Criteria for Gross Morphological Evaluations

| Characteristic | Grading | Score |
|---|---|---|
| Edge Integration (new tissue relative to native cartilage) | Full | 2 |
| | Partial | 1 |
| | None | 0 |
| Smoothness of the cartilage surface | Smooth | 2 |
| | Intermediate | 1 |
| | Rough | 0 |
| Cartilage surface, degree of filling | Flush | 2 |
| | Slight depression | 1 |
| | Depressed/overgrown | 0 |
| Color of cartilage, opacity or Translucency of the neocartilage | Opaque | 2 |
| | Translucent | 1 |
| | Transparent | 0 |

Histology and Histological Evaluation

Immediately after dissection and following gross joint surface observations, the joints were placed in 10% phosphate buffered formalin (at least ten-fold volume) for at least 48 hours. After fixation in 10% phosphate buffered formalin, the specimens were grossly trimmed to remove extra tissue.

The tissues were then decalcified in Decalcification solution made by Veterinary Pathology Services (Sodium Citrate buffered formic acid). The specimens remained in the decal solution until complete decalcification was determined. Following complete decalcification, the specimens were dehydrated through a series of ethanols and embedded in paraffin. The specimens were sectioned to 5-10 μm and one section stained with H&E and a second section stained with Safranin O and counterstained with Fast Green. For histological analysis of the sections, the scoring scale shown in Table 4 was used.

TABLE 4

Histologic Scoring Scale

| Characteristic | Grading | Score |
|---|---|---|
| I. Nature of predominant tissue | Hyaline cartilage | 4 |
| | Mostly hyaline cartilage | 3 |
| | mixed hyaline and fibrocartilage | 2 |
| | Mostly fibrocartilage | 1 |
| | some fibrocartilage, mostly nonchrondocytic cells | 0 |
| II. Structural Characteristics | | |
| A. Surface regularity | Smooth and intact | 3 |
| | superficial horizontal lamination | 2 |
| | fissures | 1 |
| | severe disruption, including fibrillation | 0 |
| B. Structural Integrity | Normal | 2 |
| | slight disruption, including cysts | 1 |
| | severe disintegration | 0 |
| C. Thickness | 100% of normal adjacent cartilage | 2 |
| | 50-100% of normal cartilage | 1 |
| | 0-50% of normal cartilage | 0 |
| D. Bonding to adjacent cartilage | Bonded at both ends of graft | 2 |
| | Bonded at one end or partially at both ends | 1 |
| | Not bonded | 0 |
| III. Freedom from Cellular Changes of Degeneration | | |
| A. Hypocellularity | Normal cellularity | 2 |
| | slight hypocellularity | 1 |
| | moderate hypocellularity or hypercellularity | 0 |
| B. Chondrocyte Clustering | No clusters | 2 |
| | <25% of the cells | 1 |
| | 25-100% of the cells | 0 |
| IV. Freedom from Degenerative Changes in Adjacent Cartilage | Normal cellularity, no clusters, normal staining | 3 |
| | Normal cellularity, mild clusters, moderate staining | 2 |
| | Mild or moderate hypocellularity, slight staining | 1 |
| | Severe hypocellularity, poor or no staining | 0 |
| V. A. Reconstitution of subchondral Bone | Normal | 3 |
| | Reduced subchondral bone reconstitution | 2 |
| | Minimal subchondral bone reconstitution | 1 |
| | No subchondral bone reconstitution | 0 |
| B. Inflammatory response in subchondral bone region | None/mild | 2 |
| | Moderate | 1 |
| | Severe | 0 |
| VI. Safranian-O Staining | Normal | 3 |
| | Moderate | 2 |
| | Slight | 1 |
| | None | 0 |
| TOTAL MAXIMUM SCORE: | Sections with Safranin-O | 28 |
| | Sections with H&E | 25 |

Note to Table 4:
In this goat study, if the tissue was scored as "4 = hyaline cartilage" it essentially consisted of only hyaline cartilage, no trace of fibrocartilage.
Scoring the nature of the repair tissue as "3 = mostly hyaline cartilage" was given to sections which had some trace of fibrocartilage, but less than 25% as determined visually.
A score of "2 = mixed hyaline and fibrocartilage" was given to repair tissue which had both hyaline and fibrous tissue, varying from approximately 75% hyaline/25% fibrous to 25% hyaline/75% fibrous.
A score of "1 = mostly fibrocartilage" was given to repair tissue which showed some traces (less than 25%) of hyaline, but was primarily fibrous in nature.
A score of "0 = some fibrocartilage, mostly non-chondrocytic" was given to repair tissue which did not exhibit any hyaline tissue at all.

Gross Morphology Results

On gross evaluation, the degenerative articular cartilage changes were well matched between the operated and contralateral knee joints. In a few cases, the degenerative changes observed in the contralateral knee were of the same score but affected a smaller area compare to the counterpart operated knee. The condyle groove junction and distal trochlear sulcus (femoral groove) showed fairly matched degenerative changes. Osteophytosis was observed in the areas level to and adjacent to the MFC lesion site. This was observed in the control treated as well as in the high and low dose groups. Historical controls have also shown this osteophytosis level to and adjacent to the defect suggesting that it due to altered biomechanics and the resultant adaptive remodeling grossly, repair tissue was detected in the MFC lesion site in 4 of 6 goats at the 12 weeks postoperation ("A" groups) time point, and in 9 of 9 sites in the MFC lesion site at 24 weeks postoperation ("B" Groups). In general, regarding the presence of repair tissue, Groups 2A, 3A, 2B and 3B did well as reflected in better gross scores. Grossly, lesions in Group 1A (Saline) were essentially graded as empty. Lesions in the longer term Group 1B (Saline) animals showed some repair tissue, presumably fibrocartilage, which helped the gross score. Slight depression of the articular cartilage surrounding the MFC lesion site was usually observed. At the 12 week time point, slight to marked depression around the MFC lesion site was seen with none of the treated defects being flush to the surrounding cartilage. The 24 week subjects showed depressions around the lesion site that grossly ranged from slight in 5 of 9 animals, marked in 2 of 9 animals and flush in 2 of 9 animals. From the histology, this appears to be due to the 6 mm depth of subchondral bone drilling in creating the defect.

The data were normalized by multiplying the initial evaluation score by the grossly estimated amount (% area) of repair tissue present. Groups 2A and 2B had the best gross response, and these were defects treated with the highest growth factor concentration. The next best were Groups 3A and 3B, which were the low dose growth factor treated lesions. At 24 weeks, there was not much difference in the normalized scores between groups since the gross area of repair tissue relative to the total lesion area was 75-100% in most cases. There was one with 50% repair (Goat 243 pink, Group 3B (AC100LD)). All animals in the 12 week Groups had a lower percentage of gross area of repair tissue relative to the total lesion area.

Histological Analysis Results

At 12 weeks, the cartilage defects treated with AC-100 Concentration A+collagen sponge exhibited slightly better healing outcomes (average score 13.5 out of a maximum score of 28) than the Control (250 µl saline+collagen sponge) and the AC-100 Concentration B+collagen sponge groups (scores 9.0 and 10.0, respectively). Filling of the cartilage defects was primarily by fibrosis/fibroplasia. In all sections examined, the implant contained one or more cystic spaces and the surface of the implant was sunken in relation to the adjacent articular surface.

For the 24 week specimens examined, cartilage defects treated with AC-100 Concentration A+collagen sponge exhibited better healing outcomes (average score 20.3 out of a maximum score of 28) than the Control (250 µl saline+ collagen sponge) and the AC-100 Concentration B+collagen sponge groups (scores 17.5-19.7* and 15.7, respectively). The value for the Control group has a range in order to prevent it from being misleading. There was one specimen that was recut and the grading was only along the edges of the defect where it grossly appeared to be cartilage flow, as the central portion of the defect was empty. Without this animal included, the score for the Control group would be 17.5, and with this animal included, the score increased to 19.7. Filling of the cartilage defects was primarily by fibrosis/fibroplasia in the deeper region of the defect, and hyaline cartilage at the articular surface. There was no evidence of an inflammatory response in any sections examined.

In summary, two different doses of AC-100 demonstrated dose dependent activities on cartilage formation in this goat osteoarthritis model. In particular, the high concentration group (4×25 mg AC-100 and collagen sponge) showed statistically significant improvements as compared to the Control group.

No adverse events were identified from either of gross observation or post-mortem histopathology analyses.

Example 4

Effect of Multiple Intra-Articular Injections and Concentrations of AC-100 in a Full-Thickness Chondral Effect Model±Microfracture: An investigation in the Goat Knee The effect of the AC-100 on intra-articular injection was evaluated on cartilage lesion healing in the goat stifle joint. AC-100 treatment significantly improved the healing of the microfractured and non-microfractured defects in a dose-dependent manner. Gross morphology raw scores were converted to normalised scores by multiplication with the % area of the defect covered with repair tissue. FIG. 5 shows normalized scores versus dosage of AC-100 in milligrams. The graph illustrates that AC-100 induces a dose-dependent regenerative effect on hard tissue growth in vivo.

Thirty-six (36) adult female goats were divided into eight (8) groups. There were two arms to the study A=microfracture of the defect and B=no microfracture of the defect. Each arm had four groups (saline; AC-100 5, 25, 125 mg per dose) A full thickness cartilage defect was created in the right hind-leg medial femoral condyle of each goat. Following closure of the joint capsule, the operated joint was injected with 1.5 ml of one of the test articles or vehicle (saline). All animals had an additional injection of the same Test Article or saline at 1, 2 and 3 weeks after surgery. On day 42 (6 weeks) after the surgery and initial injection, all animals were humanely euthanized. MR images of the joints were taken, the joints grossly evaluated for specific changes relative to the cartilage surfaces, synovial membrane and draining lymph nodes. Gross and histological analyses were performed to determine the effect on early cartilage healing, and the reactions of the synovial membrane and popliteal lymph node.

AC-100 treatment significantly improved the healing of the non-microfractured and microfractured defects. The effect of AC-100 on the microfractured defects was less significant possibly due to the higher degree of spontaneous healing.

Test Material

Test Article 1: AC-100 5 mg

| Test material name | AC-100 5 mg/injection |
| Supplier | Acologix, Inc. |
| Lot Number | 2K06028 |

Test Article 2: AC-100 25 mg

| Test material name | AC-100 25 mg/injection |
| Supplier | Acologix, Inc. |
| Lot Number | 2K06028 |

Test Article 3: AC-100 125 mg

| Test material name | AC-100 125 mg/injection |
| Supplier | Acologix, Inc. |
| Lot Number | 2K06028 |

Sham Article: Saline

| Test material name | Sterile Saline |
| Supplier | AmTech |
| Lot Number | 511471F |

Experimental Procedures

Animals

A total of 36 skeletally mature female Spanish goats were used for this study.

The goat was chosen because of the large relative stifle joint size, ease of handling and use in other viscosupplementation studies.

Animal housing conditions conformed with applicable laws and regulations relating to laboratory animals, i.e., Animal Welfare Act, Public Law 89-544 as amended in Public Law 99-198, Federal Register 52:16, United States Department of Agriculture—Animal and Plant Inspection Service (USDA-APHIS), 1985 and Public Health Service Policy on Humane Care of Laboratory Animals, Office for Protection Against Research Risks/National Institutes of Health (OPRR/NIH), September, 1986.

Treatment

The study design is shown below:

| Group | No. Right Stifle | Test Article | Sacrifice Period |
|---|---|---|---|
| 1A | 5 ACD ½ MFC Defect + MFx | AC-100 5 mg | Day 42 ± 2 |
| 2A | 5 ACD ½ MFC Defect + MFx | AC-100 25 mg | Day 42 ± 2 |
| 3A | 5 ACD ½ MFC Defect + MFx | AC-100 125 mg | Day 42 ± 2 |
| 4A | 3 ACD ½ MFC Defect + MFx | Saline | Day 42 ± 2 |
| 1B | 5 ACD ½ MFC Defect | AC-100 5 mg | Day 42 ± 2 |
| 2B | 5 ACD ½ MFC Defect | AC-100 25 mg | Day 42 ± 2 |
| 3B | 5 ACD ½ MFC Defect | AC-100 125 mg | Day 42 ± 2 |
| 4B | 3 ACD ½ MFC Defect | Saline | Day 42 ± 2 |
| Total | 36 | | |

MFx = microfracture

Surgery and Implantation

The basic procedure was identical for all subjects. All injections were performed under strict asepsis. Prior to surgery a blood sample was taken for serum analysis. Peri-injection antibiotics were dosed intramuscularly at 2.4 million units of Bicillin® at the beginning of the procedure. Brief anaesthesia was induced with a mixture of ketamine-xylazine. A standard lateral parapatellar approach to the stifle joint was made. The synovial fluid was collected and frozen for analysis. The full thickness cartilage defect (ACD½) was made at a point 10 mm distal to the medial condyle groove junction, aligned with the medial trochlear condylar ridge. The 6 mm defect was made using specialized instruments developed for the procedure. Following creation of the 6 mm full thickness defect, the joint capsule was closed. At this point, a 2-inch by 20-gauge sterile needle was introduced into the intra-articular space via an anteromedial approach. The medial wall of the lateral femoral condyle was felt and the needle backed slightly off. The appropriate volume (1.5 mL) of the appropriate Test Material was injected into the joint. The needle was removed and pressure maintained on the injection site. The subcutaneous and skin were then sutured closed in multiple layers.

At 1, 2 and 3 weeks after surgery the intra-articular injections were repeated. All injections were performed under strict asepsis. Animals were initially anesthetized with an intravenous injection of Diazepam (0.1-0.5 mg/kg) and Ketamine (4.4-7.5 mg/kg) to effect. The injection site area was shaved, prepared with betadine and alcohol scrubs using aseptic surgical techniques. Following the skin prep, the site was sprayed with 10% povidone-iodine. A standard technique was used to inject the stifle joint. A 2-inch by 21-gauge sterile needle was introduced into the intra-articular space via an anteromedial approach. The medial wall of the lateral femoral condyle was felt and the needle backed slightly off. The appropriate volume (1.5 mL) of the same Test Article as previously injected into the animal was injected into the right joint. The needle was removed and pressure maintained on the injection site. The injected stifle joint was then cycled 20-times through a full range of motion.

Post-injection checks were made for any animal displaying signs of distress and discomfort, and analgesics will be given if needed.

Necropsy

Animals were humanely sacrificed at Day 42+2 days (6 weeks). Prior to sacrifice a blood sample was taken for serum analysis. Bodyweights were recorded immediately prior to sacrifice. Deep anaesthesia was induced with a mixture of ketamine-xylazine and the subject exsanguinated according to the guidelines set forth by the AVMA Panel on Euthanasia (JAVMA, March, 2000).

The right and left hind-limbs were removed and maintained refrigerated for post-mortem Magnetic Resonance Imaging (MRI).

Following MR imaging, a gross evaluation was performed of the injected, sham and control (non-injected) stifle joints with photodocumentation. Synovial fluid was collected, evaluated for viscosity (string), and color, also smears and wet mount were made for microscopic analysis. A sample of the synovial fluid was collected into a cryovial, and frozen. The draining lymph nodes (popliteal) from each rear limb were removed, labelled, fixed in formalin, and saved for histopathological evaluation.

Gross Morphological Observations

After collection of the knee joints and post-mortem MRI, the joints were opened, photographed and the surface of the articular cartilage scored as per standard procedure documented on the necropsy sheet. The synovial membrane was examined for any inflammation. The gross morphology raw scores were converted to normalised scores by multiplication with the % area of the defect covered with repair tissue.

| Characteristic | Grading | Score |
|---|---|---|
| Edge Integration (new tissue relative to native cartilage) | Full | 2 |
| | Partial | 1 |
| | None | 0 |
| Smoothness of the cartilage surface | Smooth | 2 |
| | Intermediate | 1 |
| | Rough | 0 |
| Cartilage surface, degree of filling | Flush | 2 |
| | Slight depression | 1 |
| | Depressed/overgrown | 0 |
| Color of cartilage, opacity or Translucency of the neocartilage | Opaque | 2 |
| | Translucent | 1 |
| | Transparent | 0 |

Histology and Histological Evaluation

Immediately after dissection and following gross joint surface evaluation the following tissues were collected from the joint: posterior synovial pouch and the right medial femoral condyle. These tissues were placed in 10% phosphate buffered formalin (at least ten-fold volume) for at least 48 hours and shipped for histological processing.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating osteoarthritis, comprising:
diagnosing an area of patient as being osteoarthritic;
administering an intra-articular injection of a therapeutically effective amount of a formulation comprised of a pharmaceutically acceptable carrier and a peptide which is characterized by providing dose dependent generation of cartilage in the area;
allowing the formulation to act on the osteoarthritic area; and
examining the area of the patient to determine a change in cartilage relative to a time prior to the administering,
wherein the peptide comprises at least 20 and no more than 50 amino acid residues, wherein the sequence has the formula of DLXXXXXNDXXPFXXXXQXF (SEQ ID NO:1), wherein X is any amino acid and the peptide is further characterized by a biological activity which enhances hard tissue growth, and wherein the amino acid may be in the D- or L-configuration.

2. The method of claim 1, wherein the peptide is a peptide of SEQ ID NO:21.

3. A method of treating rheumatoid arthritis, comprising:
diagnosing a subject as suffering from rheumatoid arthritis;
determining an area of the subject as being a target area of rheumatoid arthritis disease;
administering to a subject by an intra-articular injection, a therapeutically effective amount of formulation comprising a carrier and a peptide compound of SEQ ID NO:21; and
allowing the formulation to act on the subject and treat the rheumatoid arthritis.

4. The method of claim 3, further comprising:
examining the target area of the patient to determine if cartilage has formed relative to a time prior to the administering; and
administering an additional amount of the formulation to the target area.

5. A method of treating rheumatoid arthritis, comprising:
determining an area of a rheumatoid arthritic patient in need of treatment;
administering an intra-articular injection of a therapeutically effective amount of a formulation comprised of a pharmaceutically acceptable carrier and a peptide which is characterized by providing dose dependent generation of cartilage in the area;
allowing the formulation to act on cartilage in the rheumatoid arthritic area; and
examining the area of the area to determine a change in cartilage relative to a time prior to the administering,
wherein the peptide comprises at least 20 and no more than 50 amino acid residues, wherein the sequence has the formula of (SEQ ID NO:1), wherein X is any amino acid and the peptide is further characterized by a biological activity which enhances hard tissue growth, and wherein the amino acid may be in the D- or L-configuration.

6. The method of claim 1, wherein the peptide is a peptide in the L-configuration.

7. The method of claim 2, wherein each of the chiral amino acids present in SEQ ID NO:21 is of the L-configuration.

* * * * *

SEQUENCE LISTING

<160> NUMBER OF SEQ ID NOS: 41

<210> SEQ ID NO 1
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 3, 4, 5, 6, 7, 10, 11, 14, 15, 16, 17, 19
<223> OTHER INFORMATION: Xaa = Any Amino Acid

<400> SEQUENCE: 1

Asp Leu Xaa Xaa Xaa Xaa Xaa Asn Asp Xaa Xaa Pro Phe Xaa Xaa Xaa
1               5                   10                  15

Xaa Gln Xaa Phe
        20

<210> SEQ ID NO 2
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 5, 6, 7, 10, 14, 15, 16, 17
<223> OTHER INFORMATION: Xaa = Any Amino Acid

<400> SEQUENCE: 2

Asp Leu Gln Glu Xaa Xaa Xaa Asn Asp Xaa Ser Pro Phe Xaa Xaa Xaa
1               5                   10                  15

Xaa Gln Pro Phe
        20

<210> SEQ ID NO 3
<211> LENGTH: 23
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 6, 7, 8, 11, 15, 16, 17, 18
<223> OTHER INFORMATION: Xaa = Any Amino Acid

<400> SEQUENCE: 3

Thr Asp Leu Gln Glu Xaa Xaa Xaa Asn Asp Xaa Ser Pro Phe Xaa Xaa
1               5                   10                  15

Xaa Xaa Gln Pro Phe Lys Asp
        20

<210> SEQ ID NO 4
<211> LENGTH: 20
<212> TYPE: PRT
<213> ORGANISM: Artificial Sequence
<220> FEATURE:
<223> OTHER INFORMATION: synthetic peptide

<400> SEQUENCE: 4

Asp Leu Gln Glu Arg Gly Asp Asn Asp Ile Ser Pro Phe Ser Gly Asp
1               5                   10                  15

Gly Gln Pro Phe
        20

```
<210> SEQ ID NO 5
<211> LENGTH: 20
<212> TYPE: PRT
<213> ORGANISM: Artificial Sequence
<220> FEATURE:
<223> OTHER INFORMATION: synthetic peptide

<400> SEQUENCE: 5

Asp Leu Gln Glu Asp Gly Arg Asn Asp Ile Ser Pro Phe Ser Gly Asp
 1               5                  10                  15

Gly Gln Pro Phe
            20

<210> SEQ ID NO 6
<211> LENGTH: 20
<212> TYPE: PRT
<213> ORGANISM: Artificial Sequence
<220> FEATURE:
<223> OTHER INFORMATION: synthetic peptide

<400> SEQUENCE: 6

Asp Leu Gln Glu Arg Gly Asp Asn Asp Ile Ser Pro Phe Gly Asp Gly
 1               5                  10                  15

Ser Gln Pro Phe
            20

<210> SEQ ID NO 7
<211> LENGTH: 20
<212> TYPE: PRT
<213> ORGANISM: Artificial Sequence
<220> FEATURE:
<223> OTHER INFORMATION: synthetic peptide

<400> SEQUENCE: 7

Asp Leu Gln Glu Asp Gly Arg Asn Asp Ile Ser Pro Phe Gly Asp Gly
 1               5                  10                  15

Ser Gln Pro Phe
            20

<210> SEQ ID NO 8
<211> LENGTH: 20
<212> TYPE: PRT
<213> ORGANISM: Artificial Sequence
<220> FEATURE:
<223> OTHER INFORMATION: synthetic peptide

<400> SEQUENCE: 8

Asp Leu Gln Glu Arg Asp Gly Asn Asp Ile Ser Pro Phe Ser Gly Asp
 1               5                  10                  15

Gly Gln Pro Phe
            20

<210> SEQ ID NO 9
<211> LENGTH: 20
<212> TYPE: PRT
<213> ORGANISM: Artificial Sequence
<220> FEATURE:
<223> OTHER INFORMATION: synthetic peptide

<400> SEQUENCE: 9

Asp Leu Gln Glu Arg Gly Asp Asn Asp Ile Ser Pro Phe Ser Asp Gly
 1               5                  10                  15

Asp Gln Pro Phe
            20
```

-continued

```
<210> SEQ ID NO 10
<211> LENGTH: 20
<212> TYPE: PRT
<213> ORGANISM: Artificial Sequence
<220> FEATURE:
<223> OTHER INFORMATION: synthetic peptide

<400> SEQUENCE: 10

Asp Leu Gln Glu Arg Asp Gly Asn Asp Ile Ser Pro Phe Ser Asp Gly
 1               5                  10                  15

Asp Gln Pro Phe
            20

<210> SEQ ID NO 11
<211> LENGTH: 20
<212> TYPE: PRT
<213> ORGANISM: Artificial Sequence
<220> FEATURE:
<223> OTHER INFORMATION: synthetic peptide

<400> SEQUENCE: 11

Asp Leu Gln Glu Arg Trp Asp Asn Asp Ile Ser Pro Phe Ser Gly Asp
 1               5                  10                  15

Gly Gln Pro Phe
            20

<210> SEQ ID NO 12
<211> LENGTH: 20
<212> TYPE: PRT
<213> ORGANISM: Artificial Sequence
<220> FEATURE:
<223> OTHER INFORMATION: synthetic peptide

<400> SEQUENCE: 12

Asp Leu Gln Glu Arg Trp Asp Asn Asp Ile Ser Pro Phe Gly Asp Gly
 1               5                  10                  15

Ser Gln Pro Phe
            20

<210> SEQ ID NO 13
<211> LENGTH: 20
<212> TYPE: PRT
<213> ORGANISM: Artificial Sequence
<220> FEATURE:
<223> OTHER INFORMATION: synthetic peptide

<400> SEQUENCE: 13

Asp Leu Gln Glu Arg Gly Asp Asn Asp Met Ser Pro Phe Ser Gly Asp
 1               5                  10                  15

Gly Gln Pro Phe
            20

<210> SEQ ID NO 14
<211> LENGTH: 20
<212> TYPE: PRT
<213> ORGANISM: Artificial Sequence
<220> FEATURE:
<223> OTHER INFORMATION: synthetic peptide

<400> SEQUENCE: 14

Asp Leu Gln Glu Asp Gly Arg Asn Asp Met Ser Pro Phe Ser Gly Asp
 1               5                  10                  15

Gly Gln Pro Phe
            20
```

```
<210> SEQ ID NO 15
<211> LENGTH: 20
<212> TYPE: PRT
<213> ORGANISM: Artificial Sequence
<220> FEATURE:
<223> OTHER INFORMATION: synthetic peptide

<400> SEQUENCE: 15

Asp Leu Gln Glu Arg Gly Asp Asn Asp Met Ser Pro Phe Gly Asp Gly
 1               5                  10                  15

Ser Gln Pro Phe
            20

<210> SEQ ID NO 16
<211> LENGTH: 20
<212> TYPE: PRT
<213> ORGANISM: Artificial Sequence
<220> FEATURE:
<223> OTHER INFORMATION: synthetic peptide

<400> SEQUENCE: 16

Asp Leu Gln Glu Asp Gly Arg Asn Asp Met Ser Pro Phe Gly Asp Gly
 1               5                  10                  15

Ser Gln Pro Phe
            20

<210> SEQ ID NO 17
<211> LENGTH: 20
<212> TYPE: PRT
<213> ORGANISM: Artificial Sequence
<220> FEATURE:
<223> OTHER INFORMATION: synthetic peptide

<400> SEQUENCE: 17

Asp Leu Leu Val Arg Gly Asp Asn Asp Val Pro Pro Phe Ser Gly Asp
 1               5                  10                  15

Gly Gln His Phe
            20

<210> SEQ ID NO 18
<211> LENGTH: 20
<212> TYPE: PRT
<213> ORGANISM: Artificial Sequence
<220> FEATURE:
<223> OTHER INFORMATION: synthetic peptide

<400> SEQUENCE: 18

Asp Leu Leu Val Asp Gly Arg Asn Asp Val Pro Pro Phe Ser Gly Asp
 1               5                  10                  15

Gly Gln His Phe
            20

<210> SEQ ID NO 19
<211> LENGTH: 20
<212> TYPE: PRT
<213> ORGANISM: Artificial Sequence
<220> FEATURE:
<223> OTHER INFORMATION: synthetic peptide

<400> SEQUENCE: 19

Asp Leu Leu Val Arg Gly Asp Asn Asp Val Pro Pro Phe Gly Asp Gly
 1               5                  10                  15

Ser Gln His Phe
            20
```

```
<210> SEQ ID NO 20
<211> LENGTH: 20
<212> TYPE: PRT
<213> ORGANISM: Artificial Sequence
<220> FEATURE:
<223> OTHER INFORMATION: synthetic peptide

<400> SEQUENCE: 20

Asp Leu Leu Val Asp Gly Arg Asn Asp Val Pro Pro Phe Gly Asp Gly
 1               5                  10                  15

Ser Gln His Phe
         20

<210> SEQ ID NO 21
<211> LENGTH: 23
<212> TYPE: PRT
<213> ORGANISM: Artificial Sequence
<220> FEATURE:
<223> OTHER INFORMATION: synthetic peptide

<400> SEQUENCE: 21

Thr Asp Leu Gln Glu Arg Gly Asp Asn Asp Ile Ser Pro Phe Ser Gly
 1               5                  10                  15

Asp Gly Gln Pro Phe Lys Asp
         20

<210> SEQ ID NO 22
<211> LENGTH: 23
<212> TYPE: PRT
<213> ORGANISM: Artificial Sequence
<220> FEATURE:
<223> OTHER INFORMATION: synthetic peptide

<400> SEQUENCE: 22

Thr Asp Leu Gln Glu Asp Gly Arg Asn Asp Ile Ser Pro Phe Ser Gly
 1               5                  10                  15

Asp Gly Gln Pro Phe Lys Asp
         20

<210> SEQ ID NO 23
<211> LENGTH: 23
<212> TYPE: PRT
<213> ORGANISM: Artificial Sequence
<220> FEATURE:
<223> OTHER INFORMATION: synthetic peptide

<400> SEQUENCE: 23

Thr Asp Leu Gln Glu Arg Gly Asp Asn Asp Ile Ser Pro Phe Gly Asp
 1               5                  10                  15

Gly Ser Gln Pro Phe Lys Asp
         20

<210> SEQ ID NO 24
<211> LENGTH: 23
<212> TYPE: PRT
<213> ORGANISM: Artificial Sequence
<220> FEATURE:
<223> OTHER INFORMATION: synthetic peptide

<400> SEQUENCE: 24

Thr Asp Leu Gln Glu Asp Gly Arg Asn Asp Ile Ser Pro Phe Gly Asp
 1               5                  10                  15

Gly Ser Gln Pro Phe Lys Asp
         20
```

```
<210> SEQ ID NO 25
<211> LENGTH: 23
<212> TYPE: PRT
<213> ORGANISM: Artificial Sequence
<220> FEATURE:
<223> OTHER INFORMATION: synthetic peptide

<400> SEQUENCE: 25

Thr Asp Leu Gln Glu Arg Asp Gly Asn Asp Ile Ser Pro Phe Ser Gly
 1               5                  10                  15

Asp Gly Gln Pro Phe Lys Asp
            20

<210> SEQ ID NO 26
<211> LENGTH: 23
<212> TYPE: PRT
<213> ORGANISM: Artificial Sequence
<220> FEATURE:
<223> OTHER INFORMATION: synthetic peptide

<400> SEQUENCE: 26

Thr Asp Leu Gln Glu Arg Gly Asp Asn Asp Ile Ser Pro Phe Ser Asp
 1               5                  10                  15

Gly Asp Gln Pro Phe Lys Asp
            20

<210> SEQ ID NO 27
<211> LENGTH: 23
<212> TYPE: PRT
<213> ORGANISM: Artificial Sequence
<220> FEATURE:
<223> OTHER INFORMATION: synthetic peptide

<400> SEQUENCE: 27

Thr Asp Leu Gln Glu Arg Asp Gly Asn Asp Ile Ser Pro Phe Ser Asp
 1               5                  10                  15

Gly Asp Gln Pro Phe Lys Asp
            20

<210> SEQ ID NO 28
<211> LENGTH: 23
<212> TYPE: PRT
<213> ORGANISM: Artificial Sequence
<220> FEATURE:
<223> OTHER INFORMATION: synthetic peptide

<400> SEQUENCE: 28

Thr Asp Leu Gln Glu Arg Trp Asp Asn Asp Ile Ser Pro Phe Ser Gly
 1               5                  10                  15

Asp Gly Gln Pro Phe Lys Asp
            20

<210> SEQ ID NO 29
<211> LENGTH: 23
<212> TYPE: PRT
<213> ORGANISM: Artificial Sequence
<220> FEATURE:
<223> OTHER INFORMATION: synthetic peptide

<400> SEQUENCE: 29

Thr Asp Leu Gln Glu Arg Trp Asp Asn Asp Ile Ser Pro Phe Gly Asp
 1               5                  10                  15

Gly Ser Gln Pro Phe Lys Asp
            20
```

```
<210> SEQ ID NO 30
<211> LENGTH: 23
<212> TYPE: PRT
<213> ORGANISM: Artificial Sequence
<220> FEATURE:
<223> OTHER INFORMATION: synthetic peptide

<400> SEQUENCE: 30

Thr Asp Leu Gln Glu Arg Gly Asp Asn Asp Met Ser Pro Phe Ser Gly
 1               5                  10                  15

Asp Gly Gln Pro Phe Lys Asp
            20

<210> SEQ ID NO 31
<211> LENGTH: 23
<212> TYPE: PRT
<213> ORGANISM: Artificial Sequence
<220> FEATURE:
<223> OTHER INFORMATION: synthetic peptide

<400> SEQUENCE: 31

Thr Asp Leu Gln Glu Asp Gly Arg Asn Asp Met Ser Pro Phe Ser Gly
 1               5                  10                  15

Asp Gly Gln Pro Phe Lys Asp
            20

<210> SEQ ID NO 32
<211> LENGTH: 23
<212> TYPE: PRT
<213> ORGANISM: Artificial Sequence
<220> FEATURE:
<223> OTHER INFORMATION: synthetic peptide

<400> SEQUENCE: 32

Thr Asp Leu Gln Glu Arg Gly Asp Asn Asp Met Ser Pro Phe Gly Asp
 1               5                  10                  15

Gly Ser Gln Pro Phe Lys Asp
            20

<210> SEQ ID NO 33
<211> LENGTH: 23
<212> TYPE: PRT
<213> ORGANISM: Artificial Sequence
<220> FEATURE:
<223> OTHER INFORMATION: synthetic peptide

<400> SEQUENCE: 33

Thr Asp Leu Gln Glu Asp Gly Arg Asn Asp Met Ser Pro Phe Gly Asp
 1               5                  10                  15

Gly Ser Gln Pro Phe Lys Asp
            20

<210> SEQ ID NO 34
<211> LENGTH: 23
<212> TYPE: PRT
<213> ORGANISM: Artificial Sequence
<220> FEATURE:
<223> OTHER INFORMATION: synthetic peptide

<400> SEQUENCE: 34

Pro Asp Leu Leu Val Arg Gly Asp Asn Asp Val Pro Phe Ser Gly
 1               5                  10                  15

Asp Gly Gln His Phe Met His
            20
```

```
<210> SEQ ID NO 35
<211> LENGTH: 23
<212> TYPE: PRT
<213> ORGANISM: Artificial Sequence
<220> FEATURE:
<223> OTHER INFORMATION: synthetic peptide

<400> SEQUENCE: 35

Pro Asp Leu Leu Val Asp Gly Arg Asn Asp Val Pro Pro Phe Ser Gly
1               5                   10                  15

Asp Gly Gln His Phe Met His
            20

<210> SEQ ID NO 36
<211> LENGTH: 23
<212> TYPE: PRT
<213> ORGANISM: Artificial Sequence
<220> FEATURE:
<223> OTHER INFORMATION: synthetic peptide

<400> SEQUENCE: 36

Pro Asp Leu Leu Val Arg Gly Asp Asn Asp Val Pro Pro Phe Gly Asp
1               5                   10                  15

Gly Ser Gln His Phe Met His
            20

<210> SEQ ID NO 37
<211> LENGTH: 23
<212> TYPE: PRT
<213> ORGANISM: Artificial Sequence
<220> FEATURE:
<223> OTHER INFORMATION: synthetic peptide

<400> SEQUENCE: 37

Pro Asp Leu Leu Val Asp Gly Arg Asn Asp Val Pro Pro Phe Gly Asp
1               5                   10                  15

Gly Ser Gln His Phe Met His
            20

<210> SEQ ID NO 38
<211> LENGTH: 23
<212> TYPE: PRT
<213> ORGANISM: Artificial Sequence
<220> FEATURE:
<223> OTHER INFORMATION: synthetic peptide

<400> SEQUENCE: 38

Pro Asp Leu Gln Glu Arg Gly Asp Asn Asp Ile Ser Pro Phe Ser Gly
1               5                   10                  15

Asp Gly Gln Pro Phe Lys Asp
            20

<210> SEQ ID NO 39
<211> LENGTH: 23
<212> TYPE: PRT
<213> ORGANISM: Artificial Sequence
<220> FEATURE:
<223> OTHER INFORMATION: synthetic peptide

<400> SEQUENCE: 39

Pro Asp Leu Gln Glu Asp Gly Arg Asn Asp Ile Ser Pro Phe Ser Gly
1               5                   10                  15

Asp Gly Gln Pro Phe Lys Asp
            20
```

```
<210> SEQ ID NO 40
<211> LENGTH: 23
<212> TYPE: PRT
<213> ORGANISM: Artificial Sequence
<220> FEATURE:
<223> OTHER INFORMATION: synthetic peptide

<400> SEQUENCE: 40

Pro Asp Leu Gln Glu Arg Gly Asp Asn Asp Ile Ser Pro Phe Gly Asp
 1               5                  10                  15

Gly Ser Gln Pro Phe Lys Asp
            20

<210> SEQ ID NO 41
<211> LENGTH: 23
<212> TYPE: PRT
<213> ORGANISM: Artificial Sequence
<220> FEATURE:
<223> OTHER INFORMATION: synthetic peptide

<400> SEQUENCE: 41

Pro Asp Leu Gln Glu Asp Gly Arg Asn Asp Ile Ser Pro Phe Gly Asp
 1               5                  10                  15

Gly Ser Gln Pro Phe Lys Asp
            20
```